(12) United States Patent
Manzo

(10) Patent No.: US 7,306,597 B2
(45) Date of Patent: Dec. 11, 2007

(54) ROBOTIC TOOL WITH MONOPOLAR ELECTRO-SURGICAL SCISSORS

(75) Inventor: Scott Manzo, Shelton, CT (US)

(73) Assignee: Intuitive Surgical, Inc, Sunnyvale, CA (US)

( * ) Notice: Subject to any disclaimer, the term of this patent is extended or adjusted under 35 U.S.C. 154(b) by 30 days.

(21) Appl. No.: 11/237,429

(22) Filed: Sep. 28, 2005

(65) Prior Publication Data

US 2006/0048787 A1    Mar. 9, 2006

Related U.S. Application Data

(62) Division of application No. 10/126,451, filed on Apr. 18, 2002, now Pat. No. 6,994,708.

(60) Provisional application No. 60/285,502, filed on Apr. 19, 2001.

(51) Int. Cl.
*A61B 18/18* (2006.01)
(52) U.S. Cl. ........................................................ 606/45
(58) Field of Classification Search ............... 606/1, 606/27–52; 128/898
See application file for complete search history.

(56) References Cited

U.S. PATENT DOCUMENTS 6,113,596 A * 9/2000 Hooven et al. ............... 606/42
6,436,107 B1 * 8/2002 Wang et al. ................. 606/139

* cited by examiner

*Primary Examiner*—Roy D. Gibson
*Assistant Examiner*—Pete Vrettakos

(57) ABSTRACT

The present invention provides robotic surgical instruments and systems that include electrosurgical cutting/shearing tools and methods of performing a robotic surgical procedure. The surgical instruments can advantageously be used in robotically controlled minimally invasive surgical operations. A surgical instrument generally comprises an elongate shaft having a proximal end and a distal end. An end effector, for performing a surgical operation such as cutting, shearing, grasping, engaging, or contacting tissue adjacent a surgical site, is coupleable to a distal end of the shaft. Preferably, the end effector comprises a pair of scissor-like blades for cooperatively shearing the tissue. A conductor electrically communicating with at least one blade delivers electrical energy to tissue engaged by the blades. An interface coupled to the proximal end of the shaft and removably connectable to the robotic surgical system is also included.

15 Claims, 25 Drawing Sheets

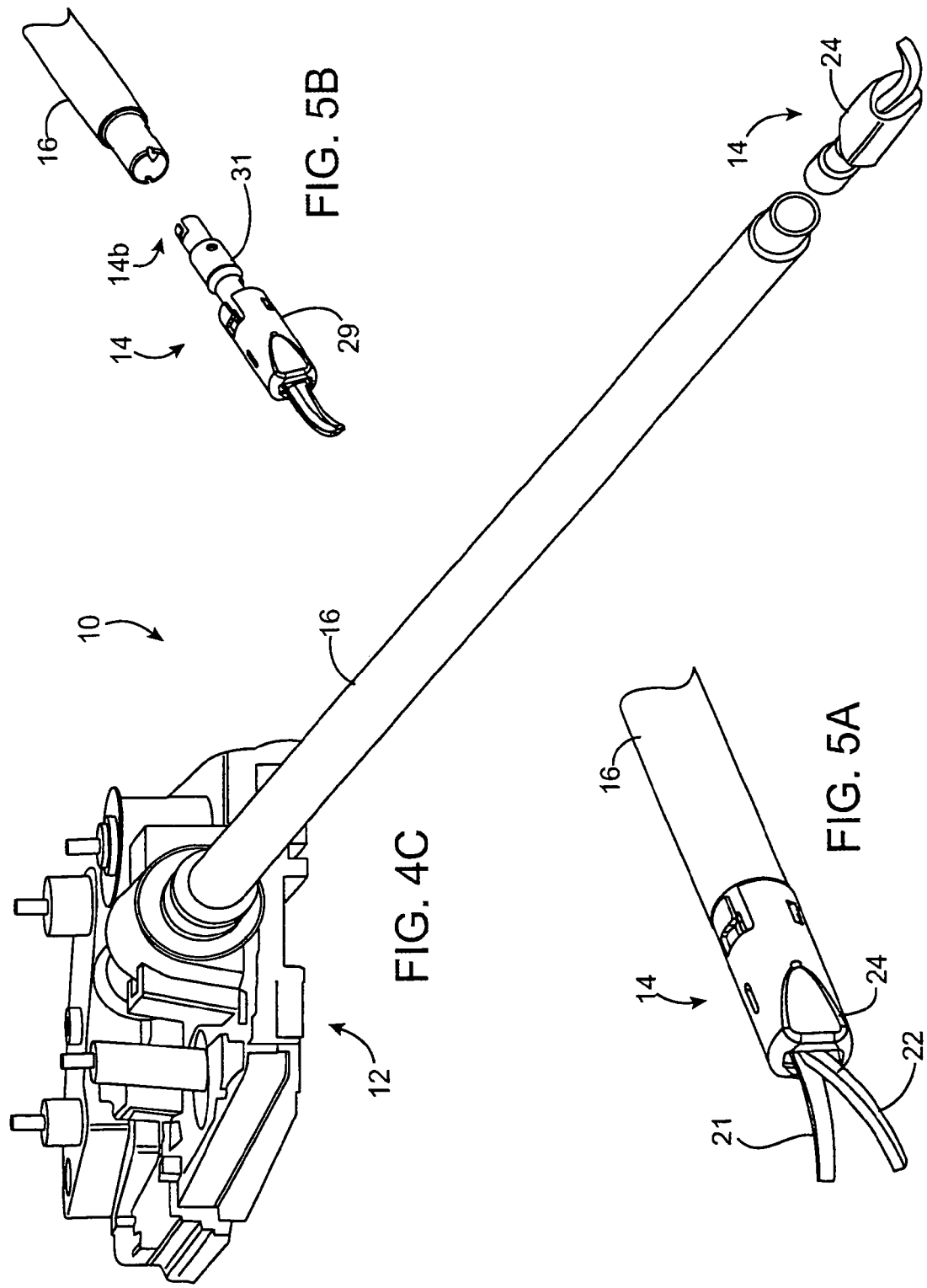

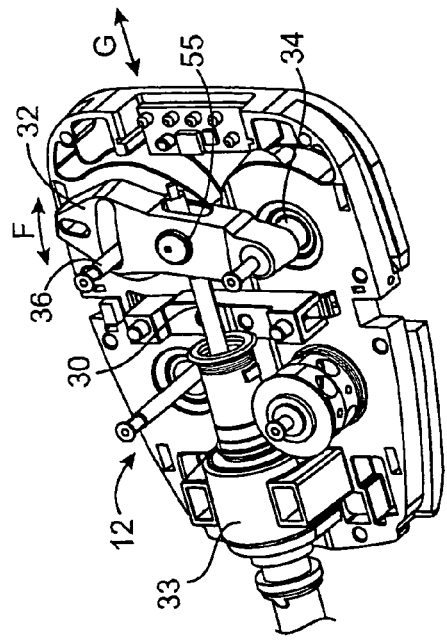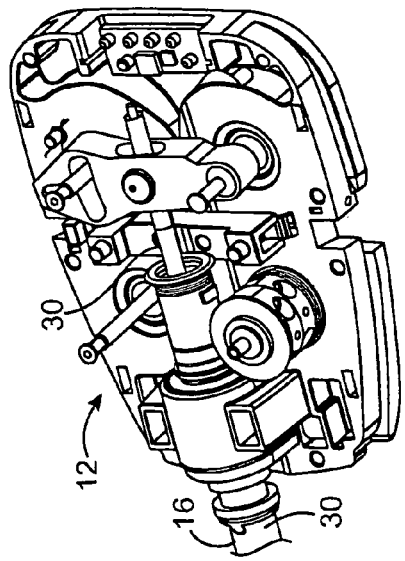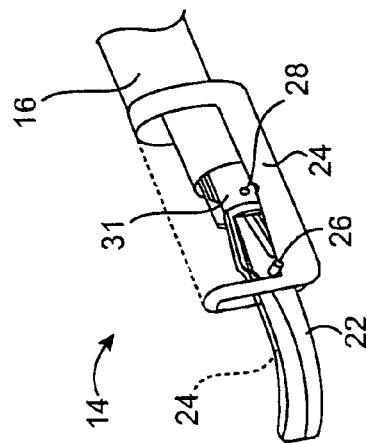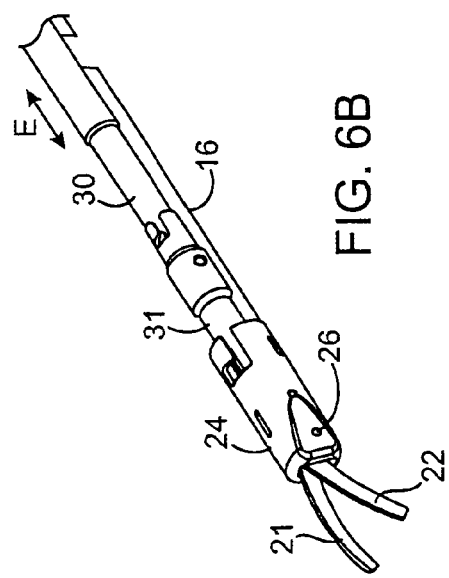
FIG. 6A
FIG. 6B
FIG. 7A
FIG. 7B

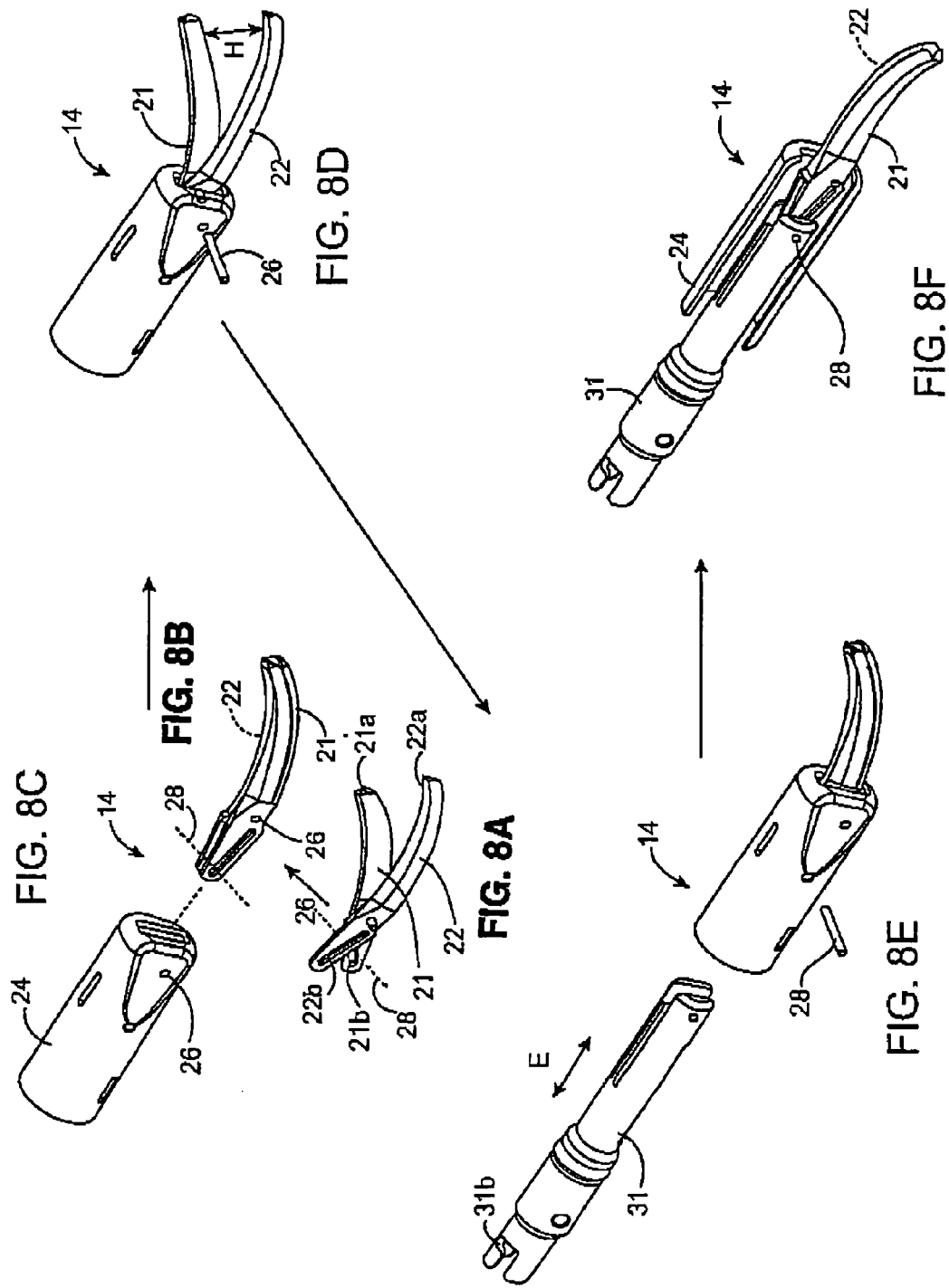

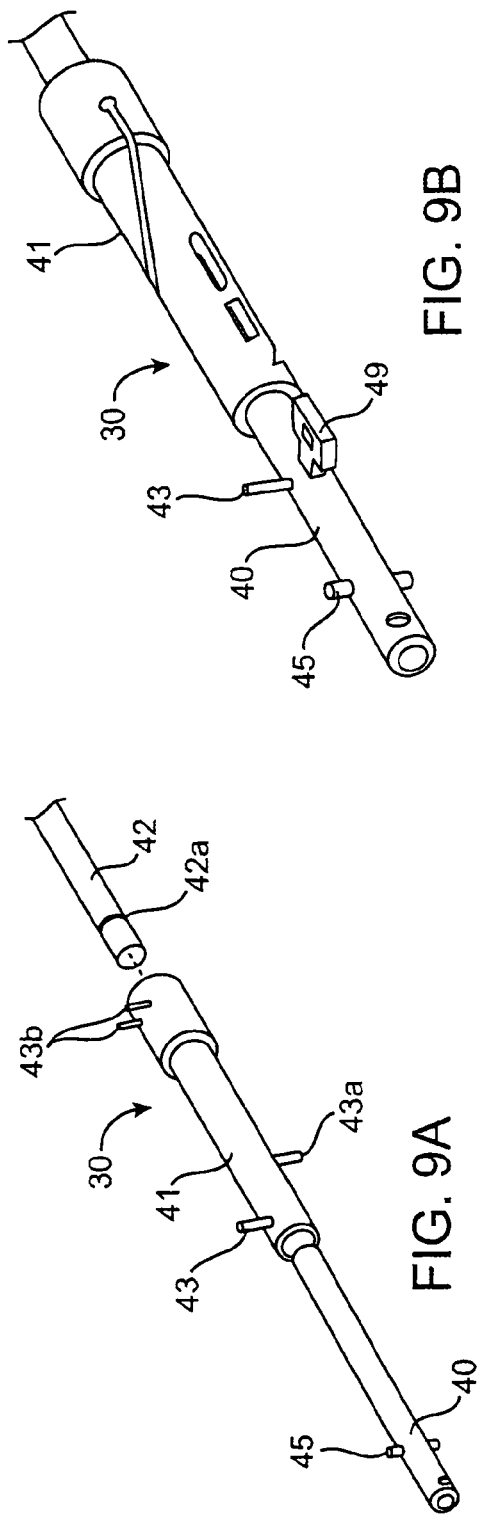

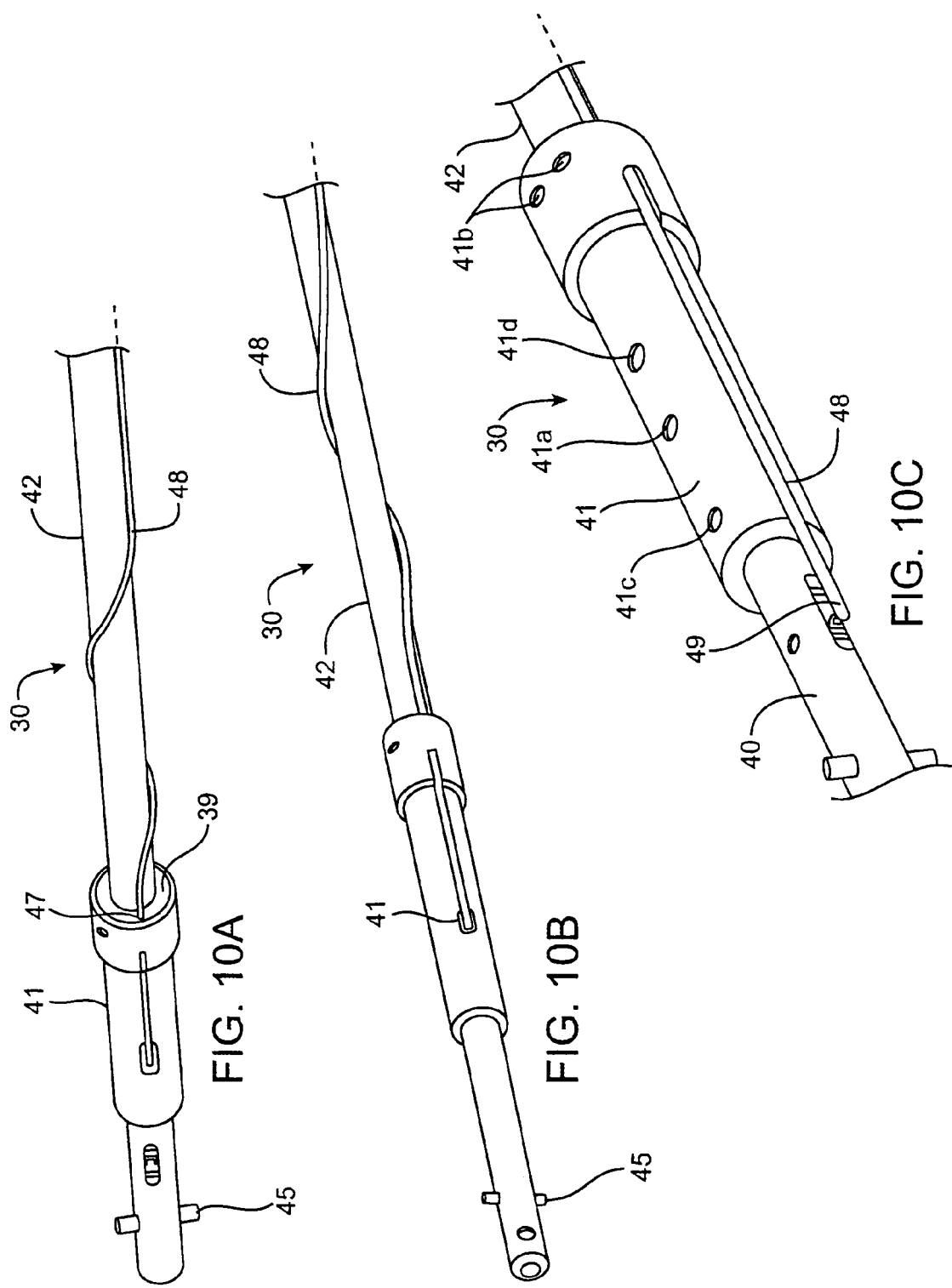

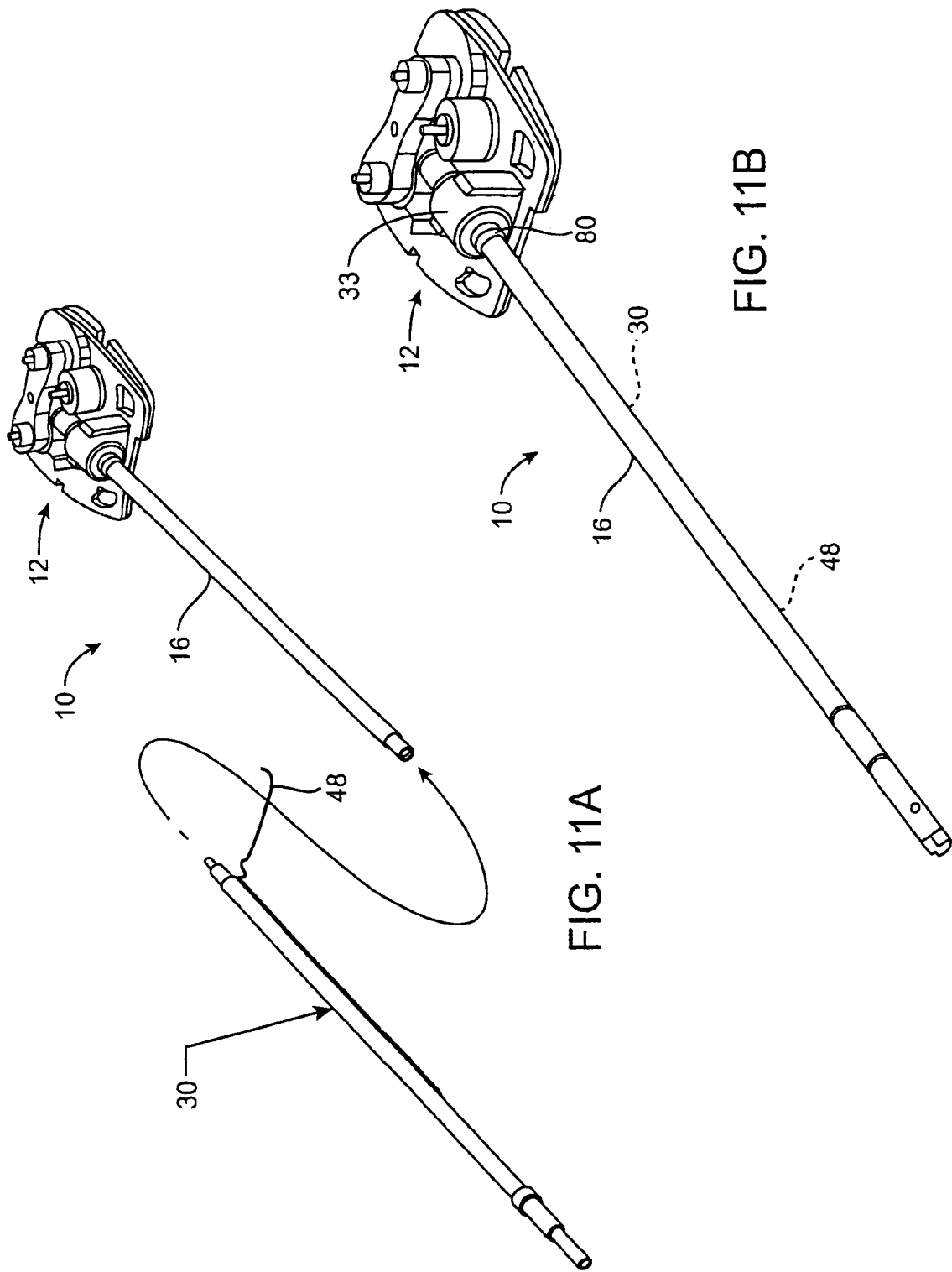

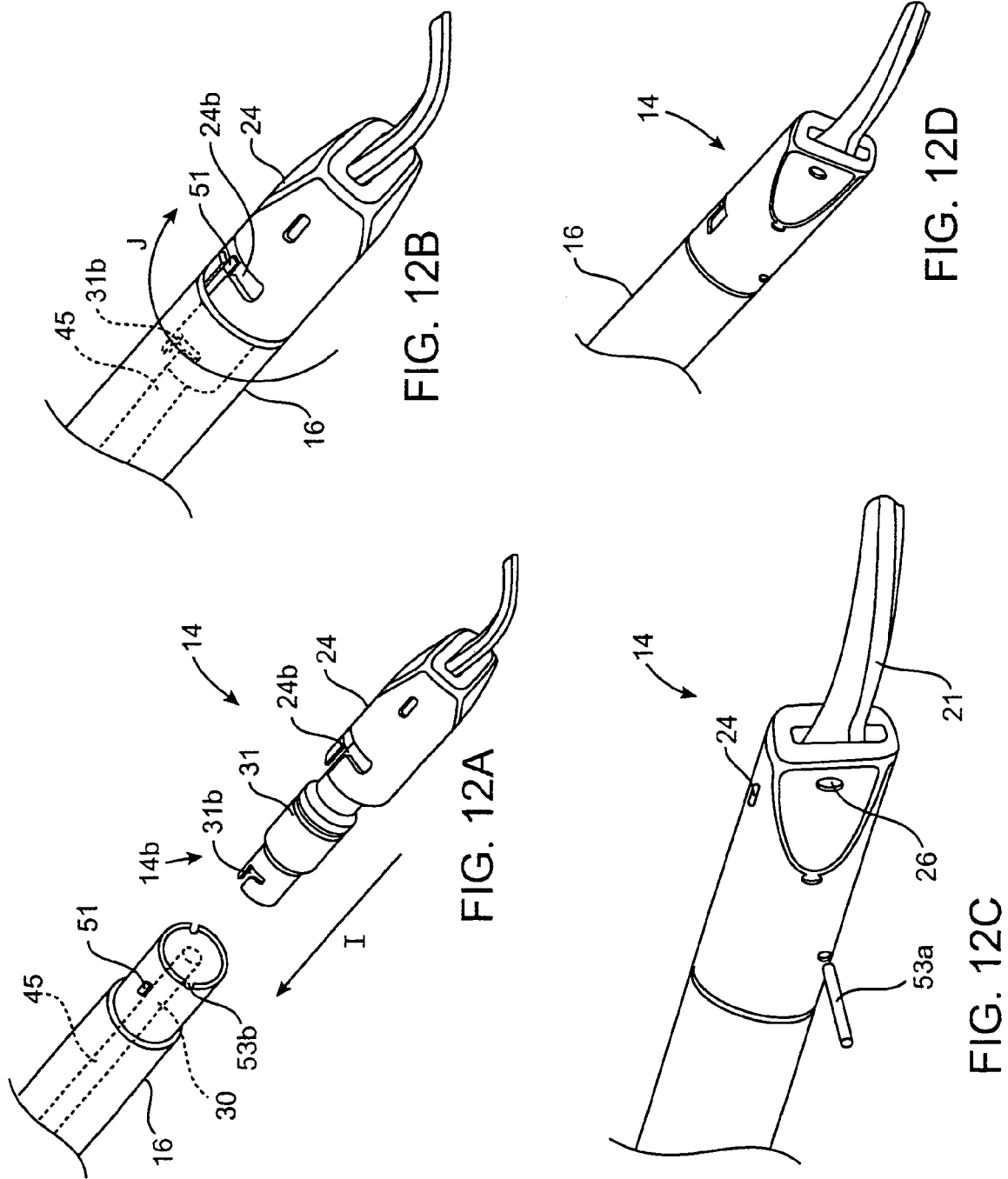

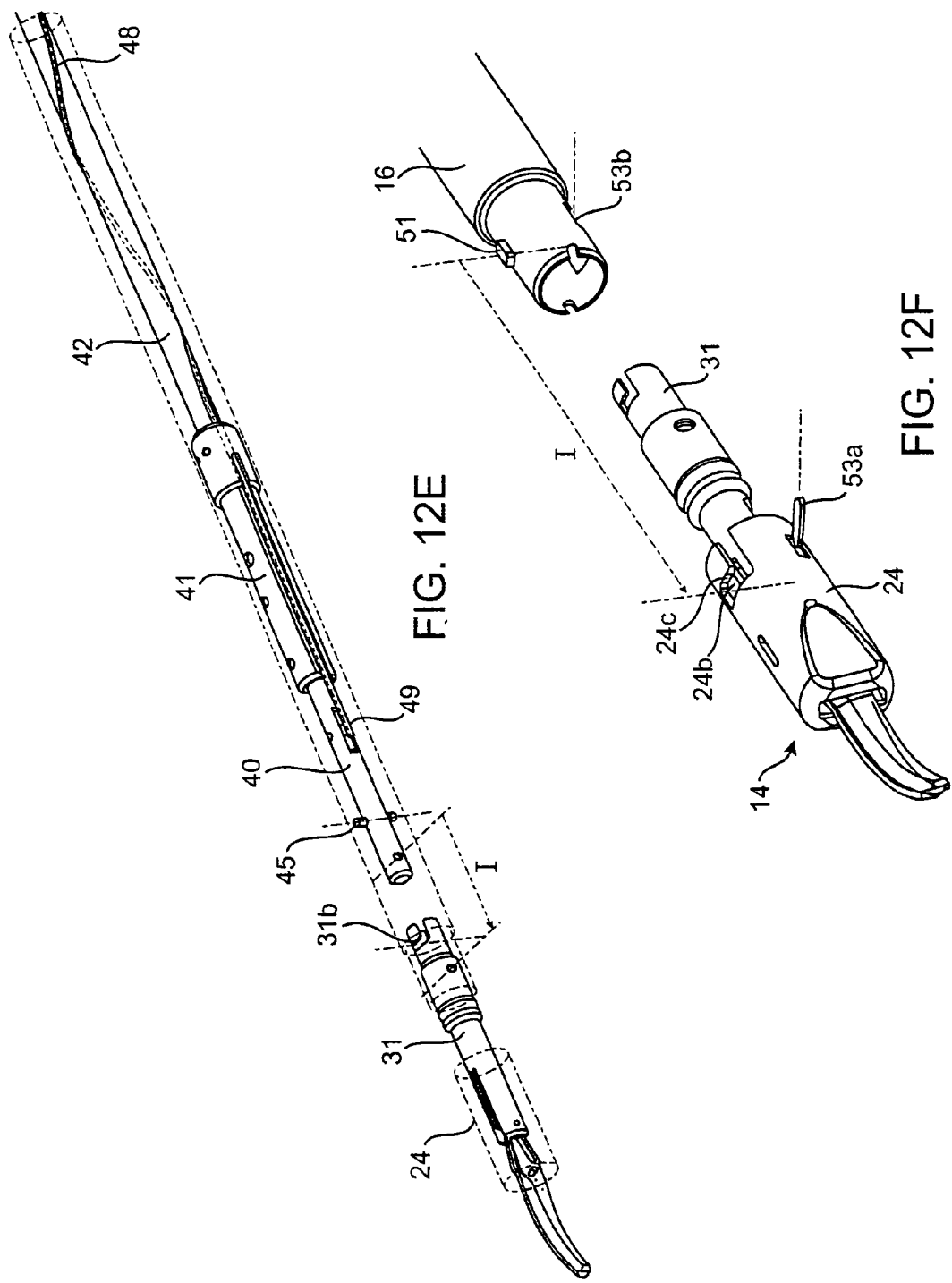

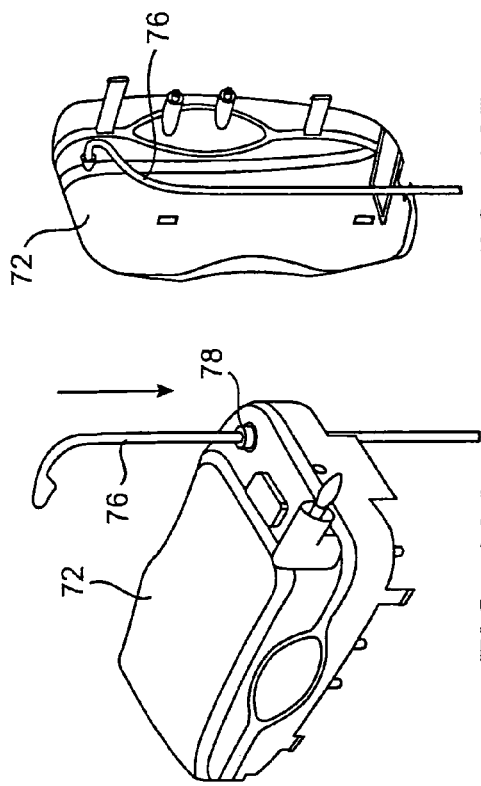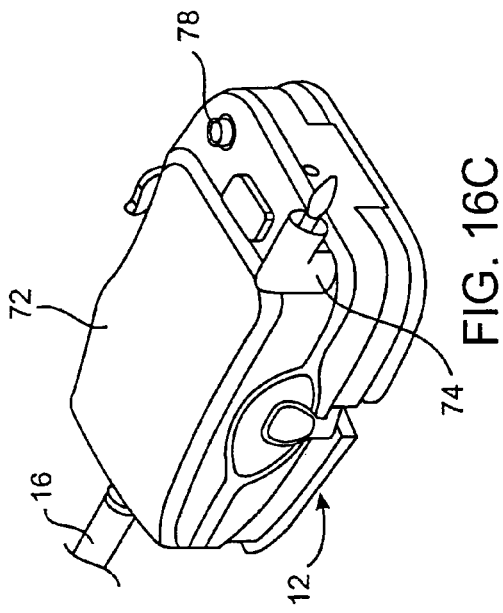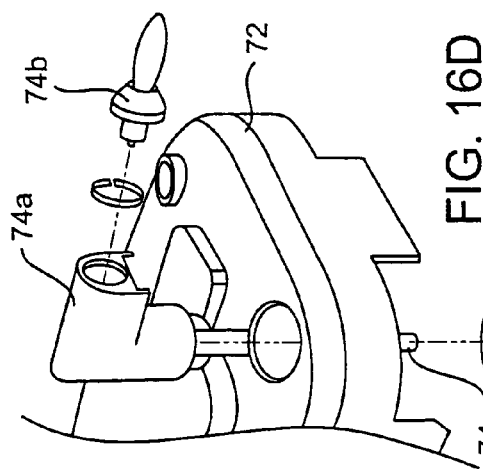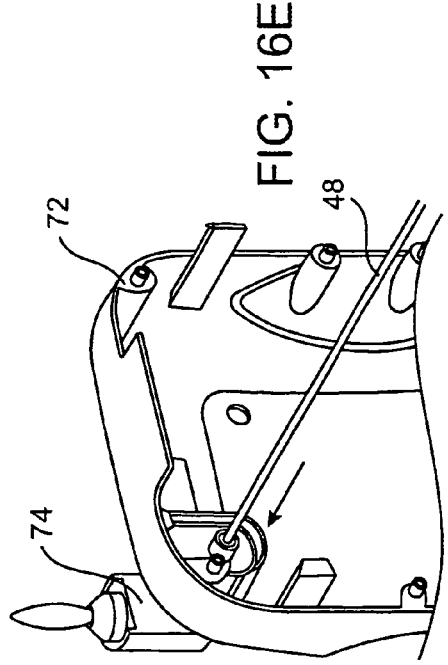
FIG. 16A
FIG. 16B
FIG. 16C
FIG. 16D
FIG. 16E

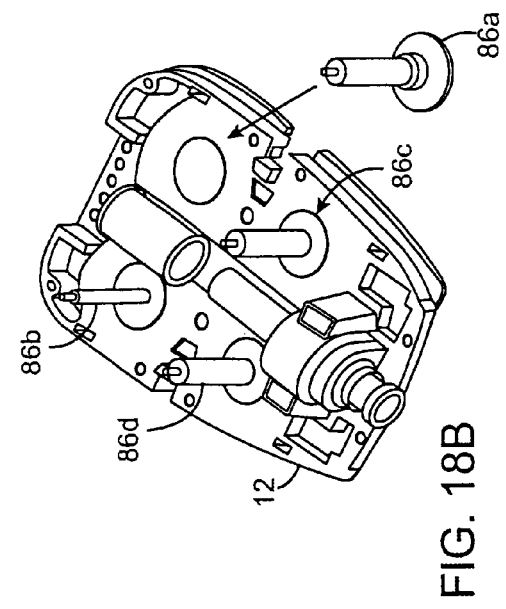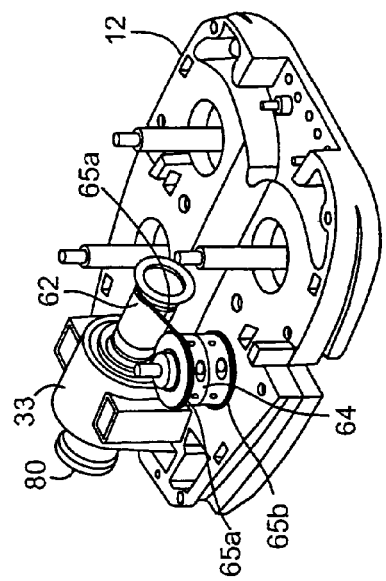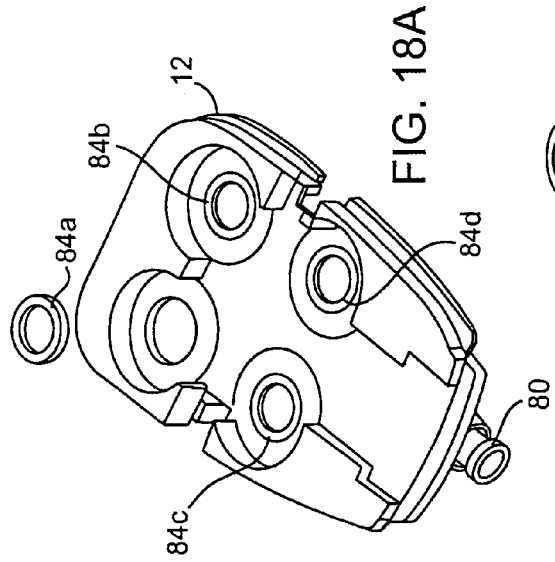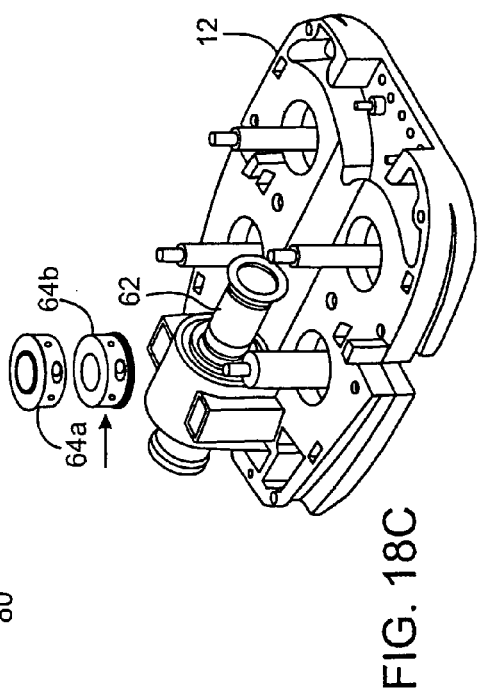

ROBOTIC TOOL WITH MONOPOLAR ELECTRO-SURGICAL SCISSORS

CROSS-REFERENCES TO RELATED APPLICATIONS

This application is a divisional application of U.S. patent application Ser. No. 10/125,451, now U.S. Pat. No. 6,994,708, which claims the benefit of priority from U.S. Provisional Application No. 60/285,502, filed on Apr. 19, 2001, under 37 C.F.R. § 1.78, the full disclosure of which is incorporated herein by reference.

This application is related to the following patents and patent applications, the full disclosures of which are incorporated herein by reference: U.S. patent application Ser. No. 10/126,499 file Apr. 18, 2002, now U.S. Pat. No. 6,783,524; U.S. Provisional Application No. 60/285,485, filed on Apr. 19, 2001, entitled "Robotic Surgical Tool With Ultrasonic Cauterizing and Cutting Instrument"; U.S. application Ser. No. 09/415,949, filed Oct. 8, 1999, entitled "Surgical Instrument With Extended Reach For Use In Minimally Invasive Surgery", now U.S. Pat. No. 6,312,435; U.S. application Ser. No. 09/626,527, filed Jul. 27, 2000, entitled "Roll-Pitch-Roll Surgical Tool", U.S. Pat. No. 6,206,903 issued Mar. 27, 2001, entitled "Surgical Tool With Mechanical Advantage", now U.S. Pat. No. 6,746,443; International Application PCT/US98/19508, filed Sep. 18, 1998, entitled "Robotic Apparatus", U.S. application Ser. No. 09/399,457, filed Sep. 17, 1999, entitled "Dynamic Association of Master and Slave in a Minimally Invasive Telesurgery System", abandoned; U.S. application Ser. No. 09/398,958, filed Sep. 17, 1999, entitled "Surgical Tools For Use In Minimally Invasive Telesurgical Applications", now U.S. Pat. No. 6,394,998; U.S. Application No. 60/116,844, filed Jan. 2, 1999, entitled "Surgical Tools For Use In Minimally Invasive Telesurgical Applications"; U.S. application Ser. No. 09/418,726, filed Dec. 6, 1999, entitled "Surgical Robotics Tools, Data Architecture, & Use", now U.S. Pat. No. 6,331,181, U.S. Application No. 60/111,713, filed Dec. 8, 1998, entitled "Surgical Instrument With Extended Reach For Use In Minimally Invasive Surgery"; U.S. Application No. 60/111,711, filed Dec. 8, 1998, entitled "Image Shifting for a Telerobotic System"; U.S. application Ser. No. 09/373,678, filed Aug. 13, 1999, entitled "Camera Referenced Control in a Minimally Invasive Surgical Apparatus", now U.S. Pat. No. 6,424,885; U.S. application Ser. No. 09/378,173, filed Aug. 20, 1999, entitled "A Stereo Imaging System and Method for Use in Telerobotic Systems", now U.S. Pat. No. 6,720,988; U.S. application Ser. No. 09/398,507, filed Sep. 17, 1999, entitled "Master Having Redundant Degrees of Freedom"; U.S. Pat. No. 5,808,665 issued Sep. 15, 1998, entitled "Endoscopic Surgical Instrument and Method for Use", now U.S. Pat. No. 6,714,839; and U.S. Pat. No. 5,976,122 issued Nov. 2, 1999, entitled "Articulated Surgical Instrument for Performing Minimally Invasive Surgery with Enhanced Dexterity and Sensitivity".

BACKGROUND OF THE INVENTION

The present invention is generally directed to surgical instruments or tools. In particular, the present invention relates to robotic surgical instruments and systems that include electrosurgical cutting/shearing tools and methods of performing a robotic surgical procedure. The surgical instruments can advantageously be used in robotically controlled minimally invasive surgical operations.

Minimally invasive surgical techniques generally reduce the amount of extraneous tissue damage during surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. Patient recovery times, patient discomfort, surgical side effects, and time away from work can also be reduced by increasing the use of minimally invasive surgery.

In theory, a significant number of surgical procedures could potentially be performed by minimally invasive techniques to achieve the advantages just described. However, only a small percentage of procedures currently use minimally invasive techniques as certain instruments, systems, and methods are not currently available in a form for providing minimally invasive surgery.

Traditional forms of minimally invasive surgery typically include endoscopy, which is visual examination of a hollow space with a viewing instrument called an endoscope. One of the more common forms of endoscopy is laparoscopy, which is visual examination and/or treatment of the abdominal cavity. In traditional laparoscopic surgery a patient's abdominal cavity is insufflated with gas and cannula sleeves are passed through small incisions in the musculature of the patient's abdomen to provide entry ports through which laparoscopic surgical instruments can be passed in a sealed fashion. Such incisions are typically about ½ inch (about 12 mm) in length.

The laparoscopic surgical instruments generally include a laparoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by a long extension tube, typically of about 12 inches (about 300 mm) in length, for example, so as to permit the surgeon to introduce the end effector to the surgical site and to control movement of the end effector relative to the surgical site from outside a patient's body.

To perform a surgical procedure, a surgeon typically passes the working tools or instruments through the cannula sleeves to the internal surgical site and manipulates the instruments from outside the abdomen by sliding them in and out through the cannula sleeves, rotating them in the cannula sleeves, levering (i.e., pivoting) the instruments against the abdominal wall, and actuating the end effectors on distal ends of the instruments from outside the abdominal cavity. The instruments normally pivot around centers defined by the incisions which extend through the muscles of the abdominal wall. The surgeon typically monitors the procedure by means of a television monitor which displays an image of the surgical site captured by the laparoscopic camera. Typically, the laparoscopic camera is also introduced through the abdominal wall so as to capture the image of the surgical site. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Although traditional minimally invasive surgical instruments and techniques like those just described have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased use of minimally invasive surgery.

Minimally invasive robotic (or "telesurgical") surgical systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient while viewing the end effector movement on the visual display during the surgical procedure. While typically viewing a three-dimensional image of the surgical site on the visual display, the surgeon performs the surgical procedures on the patient by manipulating master control devices at the remote location, which master control devices control motion of the remotely controlled instruments.

Typically, such a telesurgery system can be provided with at least two master control devices (one for each of the surgeon's hands), which are normally operatively associated with two robotic arms on each of which a surgical instrument is mounted. Operative communication between master control devices and associated robotic arm and instrument assemblies is typically achieved through a control system. The control system typically includes at least one processor which relays input commands from the master control devices to the associated robotic arm and instrument assemblies and from the arm and instrument assemblies to the associated master control devices in the case of, e.g., force feedback, or the like. An exemplary robotic surgical system is the DA VINCI™ system available from Intuitive Surgical, Inc. of Mountain View, Calif.

A typical electrosurgical treatment instrument is capable of treating tissue of an organism with the use of heat produced by electrical energy while cutting, shearing, grasping, or contacting the tissue. Such instruments are used to carry out treatments, such as incision, coagulation, and the like. Electrosurgical treatment and cutting instruments for both open surgery and manually-performed endoscopic surgery have been described. For example, both monopolar and bipolar instruments are described in U.S. Pat. No. 6,102,909, issued Aug. 15, 2000, entitled "Scissor-like Electrosurgical Cutting Instrument", the full disclosure of which is incorporated herein by reference. U.S. Pat. No. 6,132,441, issued Oct. 17, 2000, entitled "Rigidly-Linked Articulating Wrist With Decoupled Motion Transmission", and describing a robotically actuated surgical device is also incorporated herein by reference. Currently, however, electrosurgical cutting/shearing instruments for use with a robotic surgical system are not available.

Therefore, a need exists for an electrosurgical cutting/shearing instrument which permits such tissue treatments to be performed in the course of robotic minimally invasive surgery. Such an instrument would allow the advantages of electrosurgical cutting/shearing treatment and minimally invasive robotic surgery to be combined.

BRIEF SUMMARY OF THE INVENTION

The present invention provides methods, systems, and apparatus for use in robotically controlled minimally invasive surgical operations. In particular, electrosurgical cutting/shearing instruments and systems, as well as methods of performing minimally invasive robotic surgical procedures with such instruments are provided. The instruments of the present invention are capable of treating tissue with heat produced by electrical energy while cutting, shearing, grasping, engaging, or contacting treatment tissue. The electrosurgical treatment may further reduce bleeding of tissue by cauterizing tissue and coagulating blood, or achieve various other desired effects on the treatment tissue. By providing electrosurgical cutting/shearing instruments for use with a robotic surgical system, the apparatus and methods of the present invention enable the advantages associated with electrosurgical cutting/shearing treatment to be combined with the advantages of minimally invasive robotic surgery.

In a first aspect of the present invention, a surgical instrument for use with a minimally invasive robotic surgical system comprises an elongate shaft having a proximal end and a distal end. An end effector, for performing a surgical operation such as cutting, shearing, grasping, engaging, or contacting tissue adjacent a surgical site, is coupleable to a distal end of the shaft. Preferably, the end effector comprises a pair of scissor-like blades for cooperatively shearing the tissue. A conductor electrically communicating with at least one blade delivers electrical energy to tissue engaged by the blades. An interface or tool base coupled to the proximal end of the shaft and removably connectable to the robotic surgical system is also included.

Optional features may also be included in the surgical instrument. The interface generally includes at least one mechanical transmission member configured to engage a manipulator assembly of the robotic surgical system. The at least one transmission member transmits forces from the robotic surgical system to at least one actuation element coupled to the end effector so as to pivotally move at least one of the blades. The elongate shaft defines an internal longitudinally extending passage, the at least one actuation element being slidably housed within the passage to extend internally along the shaft. The at least one actuation or articulation element comprises an actuator rod coupled to a connector rod which in turn couples each blade. Actuation of the rod and connector in a distal direction relative to the shaft moves the blades apart from one another and actuation of the rod and connector in a proximal direction relative to the shaft moves the blades together in a shearing or cutting action. The at least one transmission member or interface comprises a first shaft rotatably mounted within the interface, a second shaft mounted within the interface, and a rotating link. The first shaft has two ends, at least one of the ends protruding from the interface to engage a corresponding interface member on the robotic surgical system. The rotating link is coupled to the at least one actuation element at a medial portion thereof, and engaged to the first shaft at an end portion thereof, and pivoted at the second shaft at another end portion thereof in response to rotary action of the first shaft. The rotating link is configured to longitudinally move the at least one actuation element in response to movements of the corresponding interface member and the first shaft.

The surgical instrument interface may further comprise an electrical connector for connecting the conductor to an external electrosurgical generator. Electrical energy may be supplied to the surgical instrument of the present invention by a conventional electrosurgical generator, such as the model Force F2 Electrosurgical Generator and related models made by Valley Lab of Boulder, Colo. The surgeon may activate an input, such as a foot switch electrically connected to the electrosurgical generator, causing the generator to supply electrical energy through a power cord and the connector to the instrument. Typically a high frequency AC or RF current may be employed, with the voltage being dependent on the type and degree of treatment desired. Voltages may range up to at least 12,000V in some cases, with about 3000V being a typical value, e.g., for coagulation.

The surgical instrument may further comprise a core rod slidably housed within the elongate shaft, wherein the conductor comprises an insulated conductor which extends distally from the interface to another electrical connector on a distal tip portion of the core rod. Preferably, the conductor extends in a plurality of spiral loops about the core rod to relieve stress and permit free rotation of the core rod relative to the tool interface. The core rod will usually comprise the actuator rod described above. Optionally, the core rod may comprise a separate structure apart from the actuator rod. The core tip portion engages a connector rod which in turn engages each blade. The core tip portion, connector rod, and the pair of blades are formed from conductive materials so as to provide a conduction path from the conductor to the blades.

The conduction assembly can generally provide electrosurgical treatment in a safe and effective manner that minimizes current leakage as the conductor is largely insulated from the tool base to the distal end of the shaft. The present invention incorporates a variety of safety features to prevent current leakage to non-target tissue so as to reduce collateral tissue damage, unwanted burning, or the like. In particular, an insulation sleeve may be disposed over the connector rod, the elongate shaft may comprise or be covered with an insulating material, or a housing supporting the pair of blades and connectable to the distal end of the shaft may comprise or be covered with an insulating material.

Typically, the end effector is removably coupleable to the shaft by a housing supporting the pair of blades and connectable to the distal end of the shaft. Such a bayonet assembly (housing, connector rod) which connects the end effector to the shaft and core rod conveniently permits the end effector to be easily mounted and de-mounted, e.g., for replacement or refurbishing. The elongate shaft may further be configured to rotate relative to the interface about an axis defined from the proximal end to the distal end of the elongate shaft. In such an embodiment, the interface comprises at least one shaft rotatably mounted within the interface, at least one spool being mounted on the at least one shaft, at least one cable having an upper portion and a lower portion, and a rotating member. The shaft has two ends, at least one of the ends protruding from the interface to engage a corresponding interface member on the robotic surgical system. The rotating member is coupled to the elongate shaft, wherein the upper portion of the cable wraps around the rotating member and the spool and the lower portion of the cable wraps around the spool and the rotating member in an opposite direction. The rotating member is configured to rotate the elongate shaft in response to movements of the corresponding interface member, the at least one shaft, the at least one spool, and the at least one cable.

In a second aspect of the present invention, an electrosurgical shearing instrument for use with a robotic surgical system may comprise a shaft having a proximal end and a distal end, a pair of cooperative tissue shearing blades mountable to a distal end of the shaft, and an actuation mechanism at a distal end of the shaft electrically coupled to at least one of the blades for transmitting electrosurgical energy and actuation motion. Typically, an independent electrical conductor extends along the shaft to transmit electrosurgical energy to the actuation mechanism. Further, the pair of blades and at least the distal end of the shaft are insertable and retractable through a minimally invasive surgical incision.

In a third aspect of the present invention, methods for performing minimally invasive robotic surgical procedures with the electrosurgical instruments described above are provided. One method includes connecting a surgical instrument to a robotic surgical system, passing the surgical instrument having an elongate shaft, at one end of which an end effector is mounted, through an entry port in a patient body, and engaging tissue with the end effector, the tissue being engaged between a pair of blades of the end effector. The engaged tissue may then be sheared cooperatively between the blades and electrical energy delivered to the tissue engaged by the blades. Connecting the surgical instrument to a robotic surgical system includes releasably mounting the surgical instrument on a robotically controlled arm. The methods of the present invention may further include rotating the elongate shaft relative to a tool base of the surgical instrument about an axis defined from a proximal end to a distal end of the elongate shaft.

Shearing of tissue generally comprises transmitting at least one force from the robotic surgical system to at least one actuation or articulation element coupled to the end effector and moving at least one blade with the at least one force by action of the at least one actuation element. Specifically, the transmitting and moving steps can further comprise transmitting the at least one force from an interface member on the robotic surgical system to a first rotatable shaft on the tool base of the surgical instrument. The first shaft engages a rotating link pivoted at a second shaft. The rotating link couples an actuator rod. The actuator rod engages a connecting rod. The connecting rod engages each blade. The at least one force causes the first shaft and link to rotate, causing the actuator rod and connector rod to move at least one of the blades.

Delivering electrical energy can comprise transmitting electrical energy to at least one blade from a conductor by connecting an external electrosurgical generator to the conductor. Unintended current leakage can be minimized or prevented by insulating the conductor within the elongate shaft and by extending the conductor to a distal tip of a core rod slidably housed within the shaft. The distal tip of the rod engages a connector rod which in turn engages each blade. The distal tip of the rod and connector rod transmit electrical energy to the at least one blade from the conductor. Unintended current leakage can be further prevented by insulating the connector rod within a housing supporting the pair of blades and connectable to a distal end of the shaft and/or by insulating the connector rod with an insulation sleeve.

Electrical energy delivery may be carried out before, during, and/or after tissue shearing. The delivered electrical energy produces heat capable of treating the tissue. For example, the heat may cauterize the tissue or coagulate blood so as to minimize bleeding during a treatment procedure. Preferably, electrical energy delivery is carried out in a monopolar fashion, although in certain circumstances, the principles of the present invention may be modified to include alternative instruments having bipolar electrodes. Monopolar and bipolar devices may use radio frequency (RF) energy to provide the heat necessary for cauterization and coagulation. Monopolar devices are typically used in conjunction with a grounding pad wherein one pole of an electrosurgical generator is mounted to the instrument and other pole is mounted to the grounding pad. The electrical current in monopolar devices travels from the instrument through the patient's body to the grounding pad. Bipolar instruments are typically connected to both poles of the electrosurgical generator. Current flow in bipolar devices is typically limited to tissue adjacent to the working end of the bipolar instrument.

In a forth aspect of the present invention, robotic surgical systems are provided comprising a robotic arm having an instrument holder, an electrosurgical shearing instrument detachably mountable on the instrument holder, and an electrosurgical generator. The electrosurgical shearing instrument has a proximal portion for engaging the instrument holder, an elongate shaft extending from the proximal portion to a distal end, a pair of cooperative tissue shearing blades mountable to the distal end of the shaft, and a conductor electrically communicating with at least one blade. The conductor delivers electrosurgical energy to tissue engaged by the blade and is coupled to an electrical connector on the proximal portion. The electrosurgical generator is detachably connected to the connector of the proximal portion so as to transmit electrosurgical energy distally to the at least one blade.

A further understanding of the nature and advantages of the present invention will become apparent by reference to the remaining portions of the specification and drawings.

BRIEF DESCRIPTION OF THE DRAWINGS

FIGS. 4A-4C illustrate an exemplary electrosurgical shearing instrument constructed in accordance with the principles of the present invention.

FIGS. 5A-5D illustrate exploded views of a distal portion of the instrument of FIG. 4A.

FIGS. 6A and 6B illustrate exploded views of both proximal and distal portions of the instrument of FIG. 4A with blades of the instrument in an open configuration.

FIGS. 7A and 7B illustrate exploded views of both proximal and distal portions of the instrument of FIG. 4A with the blades of the instrument in an closed configuration.

FIGS. 8A-8H illustrate the bayonet assembly of the distal portion of the instrument of FIG. 4A.

FIGS. 9A-9C and 10A-10C illustrate a core assembly of the of the instrument of FIG. 4A.

FIGS. 11A and 11B illustrate core assembly positioning within a shaft passage of the instrument of FIG. 4A.

FIGS. 12A-12F illustrate further the bayonet assembly of the distal portion of the instrument of FIG. 4A.

FIGS. 16A-16E illustrate further exploded views of the proximal portion of the instrument of FIG. 4A, with a cover over the tool base.

FIGS. 17A-17D, 18A-18D, and 19A-19D are perspective illustration of the tool base in progressive stages of assembly.

DETAILED DESCRIPTION OF THE INVENTION

The present invention provides methods, systems, and apparatus for use in robotically controlled minimally invasive surgical operations. In particular, electrosurgical cutting/shearing instruments and systems, as well as methods of performing minimally invasive robotic surgical procedures with such instruments are provided. The instruments of the present invention are capable of treating tissue with heat produced by electrical energy while cutting, shearing, grasping, engaging, or contacting treatment tissue. The electrosurgical treatment may further reduce bleeding of tissue by cauterizing tissue and coagulating blood, or achieve various other desired effects on the treatment tissue. The electrosurgical treatment is carried out in a safe and effective manner that incorporates a variety of safety features to prevent current leakage to non-target tissue so as to reduce collateral tissue damage, unwanted burning, or the like.

Figure 1:
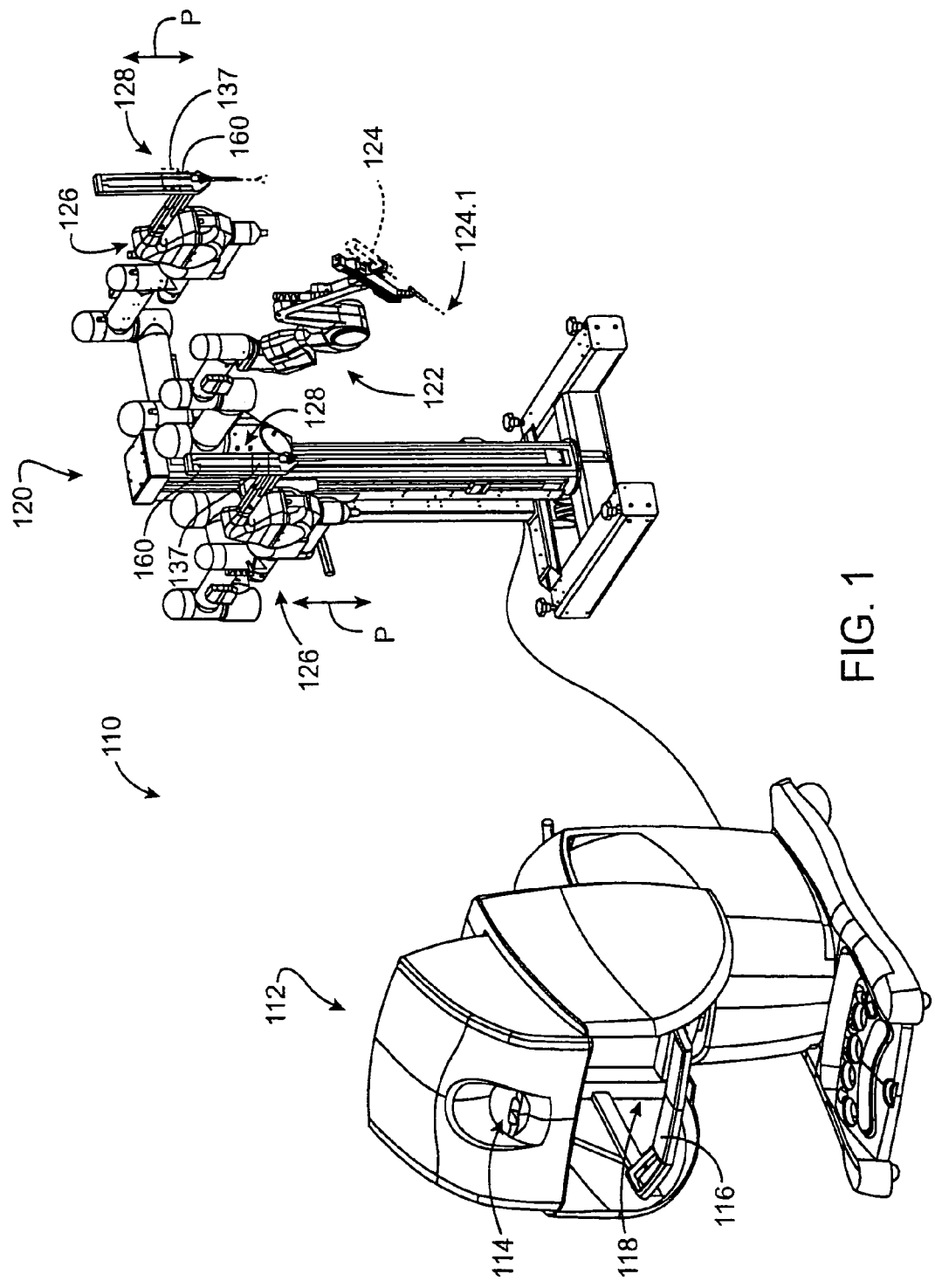
FIG. 1 is a perspective illustration of a robotic surgical system with which various embodiments of the present invention may be used.

Referring now to FIG. 1, a robotic surgical system 110 generally includes a user-operated control station or "surgeons console" 112 and a surgical work station or "cart" 120. The control station 112 includes an image display module 114 for displaying an image of a surgical site, a support 116 on which an operator may rest his/her forearms, and a space 118 where two master control devices are located (not shown). When using control station 112, a surgeon or other user typically sits in a chair in front of control station 112, views the surgical site through the display module 114, and grips the master controls one in each hand while resting the forearms on support 116. An exemplary robotic surgical system as described in FIG. 1 is the DA VINCI™ system available from Intuitive Surgical, Inc. of Mountain View, Calif.

Control station 112 is generally coupled to cart 120 such that commands from the master controls may be transmitted to the cart 120. In use, cart 120 is positioned adjacent a patient requiring surgery and is then normally caused to remain stationary until a surgical procedure to be performed by means of surgical system 110 has been completed. Cart 120 typically has wheels or castors to render it mobile. Control station 112 is typically positioned remote from cart 120 and in some embodiments may be separated from cart 120 by a great distance, for example miles away, but will typically be used within an operating room with the cart 120.

In various embodiments, cart 120 includes at least three robotic arm assemblies 122, 126, 126, one of which is configured to hold an image capture device 124 and the others of which are configured to hold surgical instruments 128. Alternatively, the cart may include more or fewer than three robotic arm assemblies and the robotic arm assemblies may be configured to hold any suitable tool, instrument, imaging device and/or the like. Image capture device 124 may include any suitable device, such as an endoscope, fiber optic camera, or the like. Image capture device 124 generally includes an object viewing end 124.1 at a remote end of an elongate shaft configured to enable the viewing end 124.1 to be inserted through an entry port in a patient's body to capture an image of the surgical site.

Coupling of cart 120 to control station 112 generally enables display module 114 to display an image captured by image capture device 124. Coupling of cart 120 to control station 112 also typically allows each of the master controls on the control station 112 (not shown) to control one robotic arm assembly 126 and one surgical instrument 128. In various embodiments, each master control may alternatively be used to control more than one robotic arm assembly 126 and/or more than one surgical instrument 128.

Surgical instruments 128 on the robotic arm assemblies 126 typically include elongate shafts, with proximal and distal ends. End effectors are generally mounted on wrist-like mechanisms pivotally mounted on the distal ends of the shafts, for enabling the instruments 128 to perform one or more surgical tasks. Generally, the elongate shafts of surgical instruments 128 allow the end effectors to be inserted through entry ports in a patient's body so as to access the internal surgical site. Movement of the end effectors is generally controlled via master controls on the control center 112.

Figure 2:
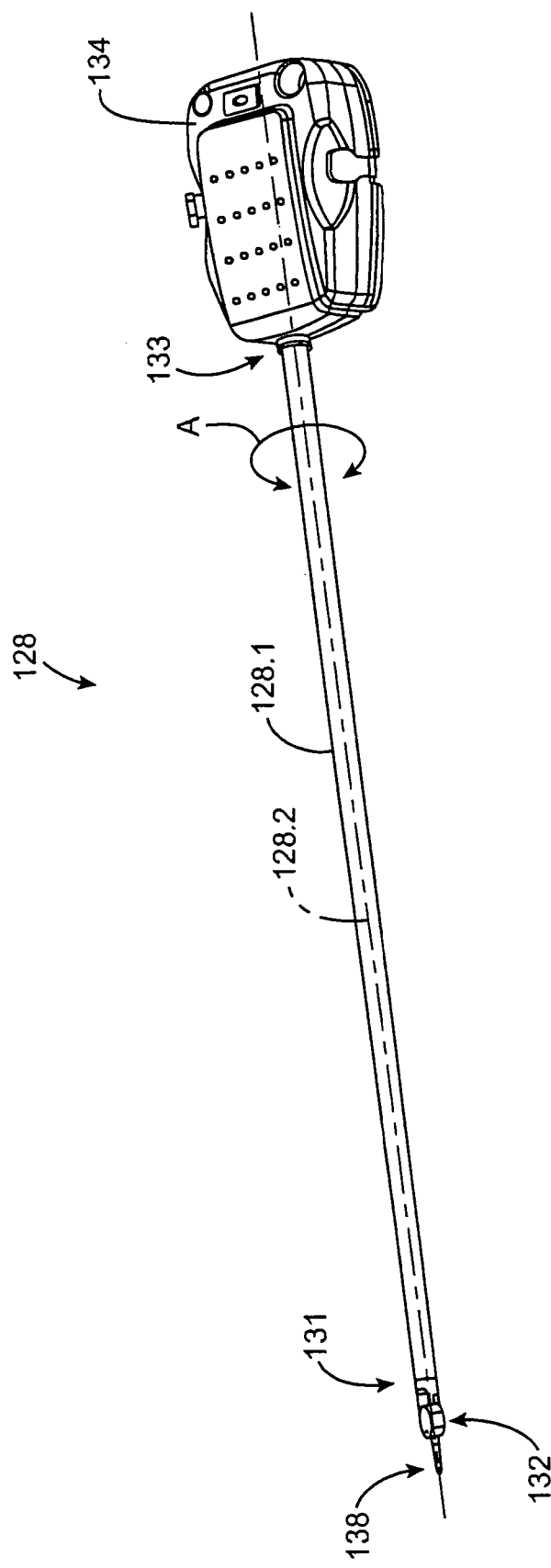
FIG. 2 is a perspective illustration of a robotic surgical tool which may be used with the robotic surgical system of FIG. 1.

Referring now to FIG. 2, surgical instrument 128 generally includes an elongate shaft 128.1 having a proximal end 133 and a distal end 131, a pivot 132, an end effector 138 disposed at the distal end, and an instrument base 134 disposed at the proximal end. Base 134 is generally configured to releasably engage an interface member of the robotic surgical system, such as robotic surgical system 110 in FIG. 1. In general, instrument 128 is engaged with the system via base 134 (base not shown in FIG. 1) such that instrument 128 is releasably mountable on a carriage 137 which can be driven to translate along a linear guide formation 160 of the arm 126 in the direction of arrows P.

Figure 3:
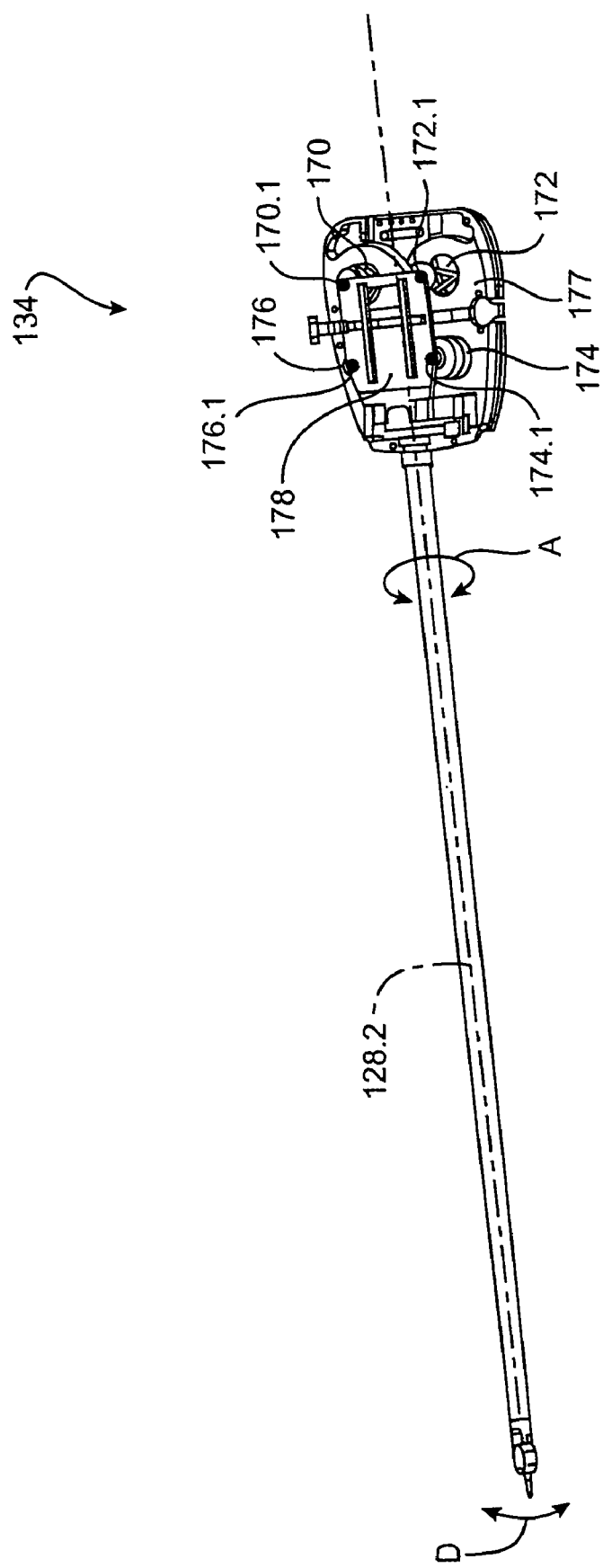
FIG. 3 is a perspective illustration of the robotic surgical tool in FIG. 2, with a cover of a tool base removed to show internal structures of the tool base.

With reference to FIGS. 2 and 3, shaft 128.1 is rotatably mounted on base 134 for rotation about an axis 128.2 extending longitudinally along the shaft 128.1 as indicated by the arrows A. Thus, when mounted on an arm assembly 126, end effector 138 may have a plurality of degrees of freedom of movement relative to manipulator arm 126, in addition to actuation movement of the end effector itself. The instrument may be translated along an insertion axis (Arrows P in FIG. 1). Typically, the instrument degrees of freedom include rotation about the axis 128.2 as indicated by arrows A, and in the case of instruments 128 including pivots 132, angular displacement as a whole about pivot 132 as indicated by arrows D. Alternatively, the distal pivoting degree of freedom may be omitted. A single pivot wrist, a multi-pivot wrist, a distal roll joint mechanism, or other joints or wrist-like mechanisms may be included to provide additional operational degrees of freedom to the end effector. Movement of end effector 138 relative to manipulator arm 126 controlled by appropriately positioned actuators, such as electric motors, or the like, which respond to inputs from an associated master control at the control station 112, so as to drive the end effector 138 to a required orientation as dictated by movement of the associated master control.

Referring now to FIG. 3, base 134 of surgical instrument 128 suitably includes transmission members 170, 172, 174, and 176, which include spools secured on shafts 170.1, 172.1, 174.1, and 176.1. Ends of shafts 170.1, 172.1, 174.1, 176.1 generally extend from a side 177 of base 134 to a mounting plate 178 within base 134 and are configured to rotate. Generally, the ends of shafts 170.1, 172.1, 174.1, 176.1 at side 177 of base 134 extend through side 177, to an outer surface of side 177 (not shown). At the outer surface, each shaft 170.1, 172.1, 174.1, 176.1 includes an engaging member (not shown) configured to releasably couple with a complementary engaging member (not shown) rotatably mounted on the carriage 137 of a robotic arm assembly 126 (see FIG. 1). The engaging members on carriage 137 are generally coupled to actuators (not shown), such as electric motors or the like, to cause selective angular displacement of each engaging member on the carriage 137 in response to actuation of its associated actuator. Thus, selective actuation of the actuators is transmitted through the engaging members on the carriage 137, to the engaging members on the opposed ends of the shafts 170.1, 172.1, 174.1, 176.1 to cause selective angular displacement of the spools 170, 172, 174, 176. Where more or fewer degrees of freedom are desired, the number of spools may be decreased or increased.

FIGS. 4-19 show an exemplary embodiment of a robotic electrosurgical shearing tool 10 constructed in accordance with the principles of the present invention. The following depictions are for illustration purposes only and do not necessarily reflect the actual shape, size, or dimensions of the robotic electrosurgical shearing instrument 10.

Figure 4A:
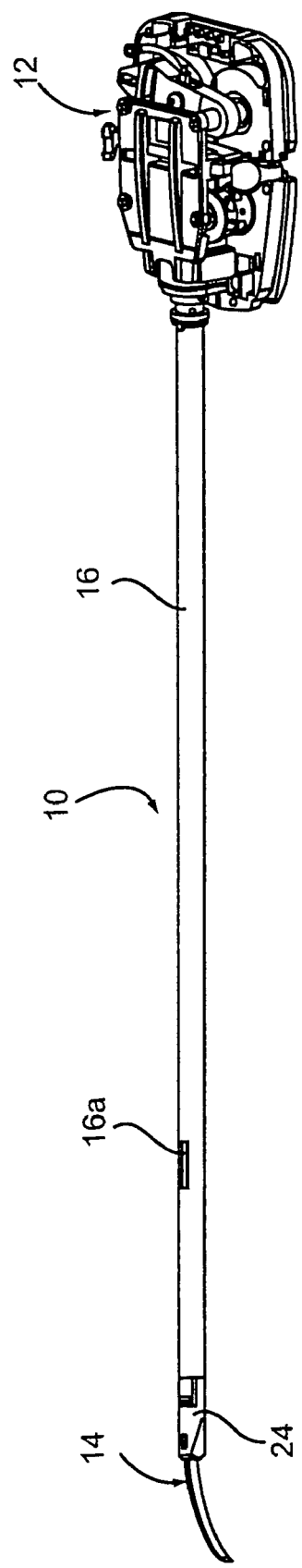
Figure 4B:
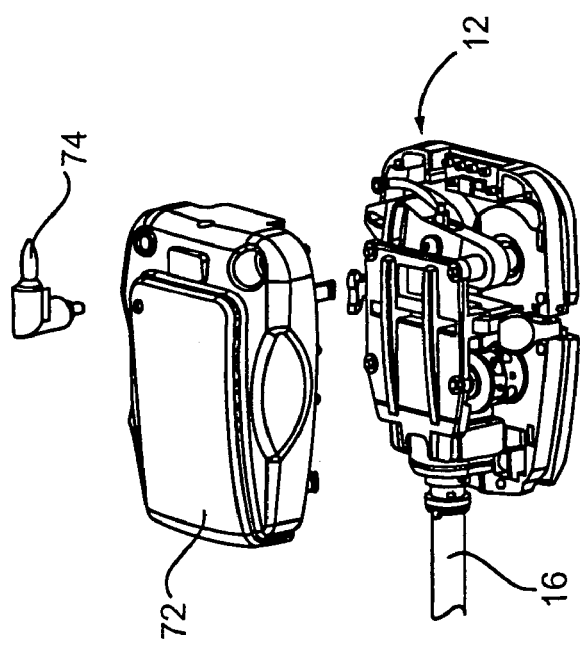
Figure 5C:
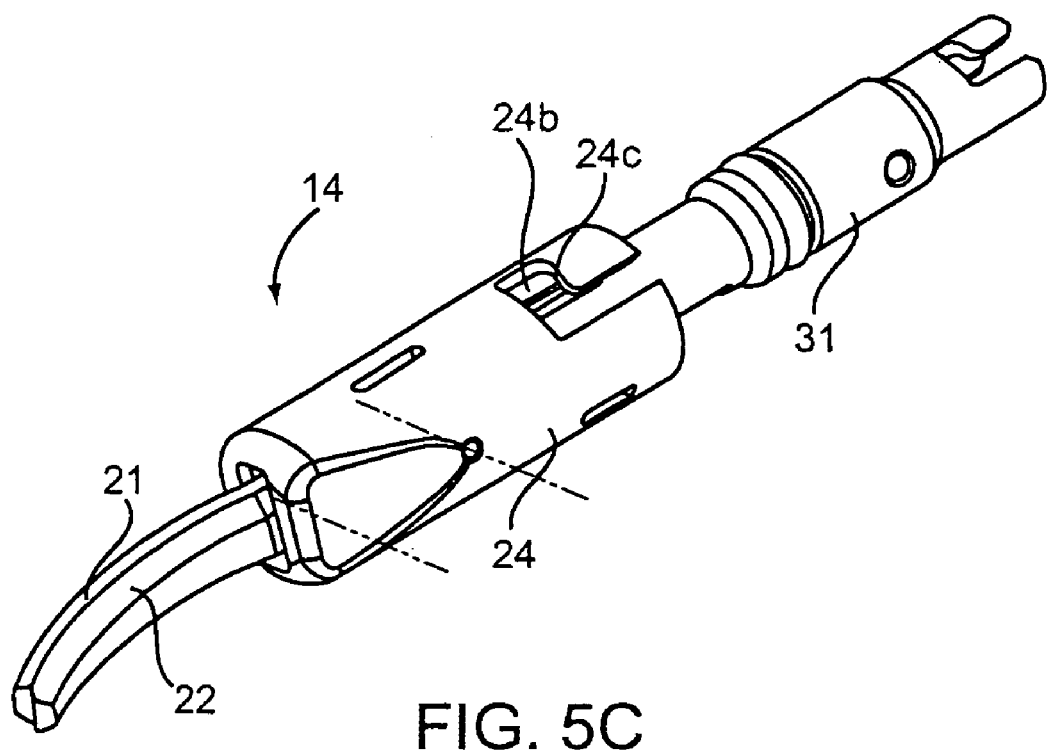
Figure 5D:
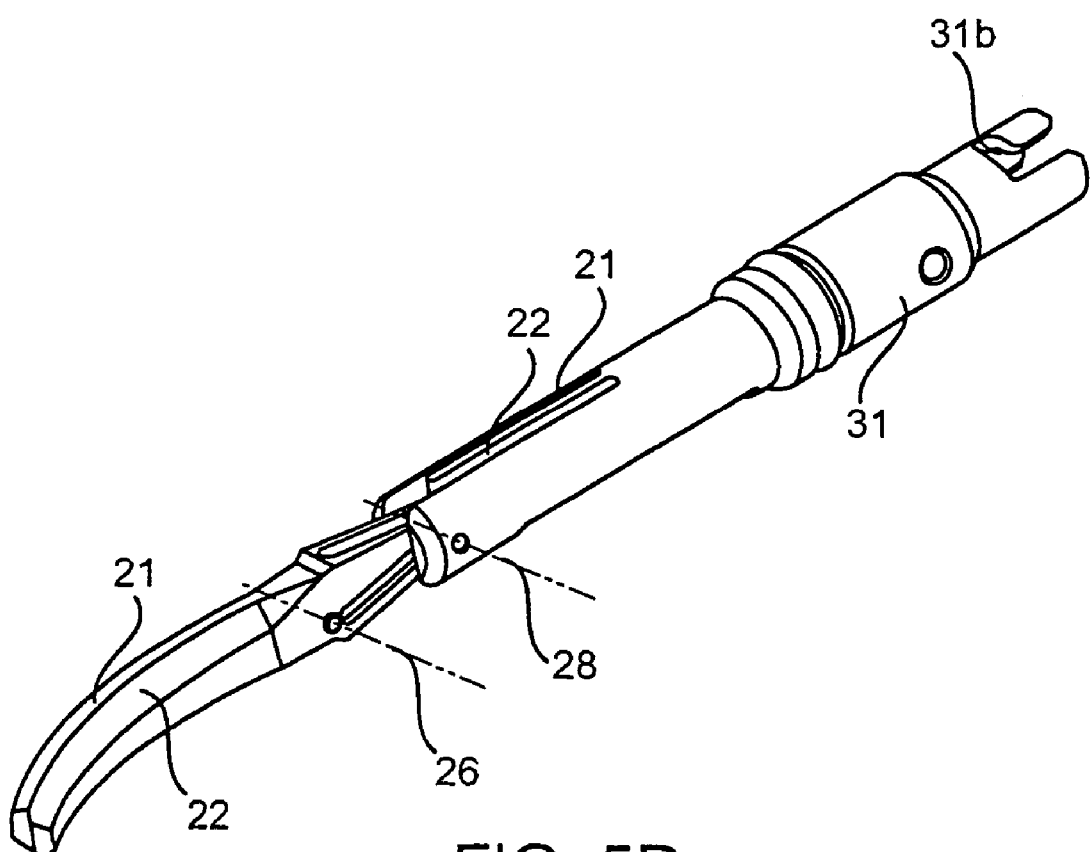

Referring now to FIGS. 4A-4C, a surgical instrument 10 for use with the minimally invasive robotic surgical system of FIG. 1 comprises an elongate shaft 16 having a proximal end and a distal end. An end effector assembly 14, for performing a surgical operation such as cutting, shearing, grasping, engaging, or contacting tissue adjacent a surgical site, is mounted at a distal end of the shaft. Preferably, the end effector 14 comprises a pair of scissor-like blades for cooperatively shearing the tissue. A conductor electrically communicating with at least one blade delivers electrical energy to tissue engaged by the blades. An interface or tool base 12 coupled to the proximal end of the shaft and removably connectable to the robotic surgical system is also included. As shown in FIG. 4B, the tool base 12 may be enclosed by a cover 72 which mounts an electrical connector 74 for the conductor to permit connection to an electrosurgical generator, as will be described in more detail below.

With reference to FIGS. 5A-5D, exploded views of the distal portion of the shaft 16 of the instrument 10 are illustrated. Generally, the end effector assembly 14 includes a tip housing 24 supporting an opposed pair of scissors blades 21 and 22. The scissor blades 21 and 22 lie generally parallel to each other with sliding contact to cause a shearing engagement of the blades. The end effector 14 mounts to shaft 16 by engagement of bayonet assembly 14b with the distal end of the shaft 16, as described in more detail below with respect to FIGS. 12A-12F.

Referring now to FIGS. 6A and 6B, exploded views of proximal and distal portions of the instrument 10 are illustrated, showing the blades 21 and 22 in an open configuration. FIGS. 7A and 7B illustrate the blades 21 and 22 in a closed configuration. Generally, the bayonet assembly upon engagement serves to couple a distal connector rod 31 to a core rod assembly 30, which is slidably housed within shaft 16. The blades 21, 22 are co-axially pivoted to tip housing 24 by means of pivot pin 26, which pivots the blades about a medial point.

Figure 8G:
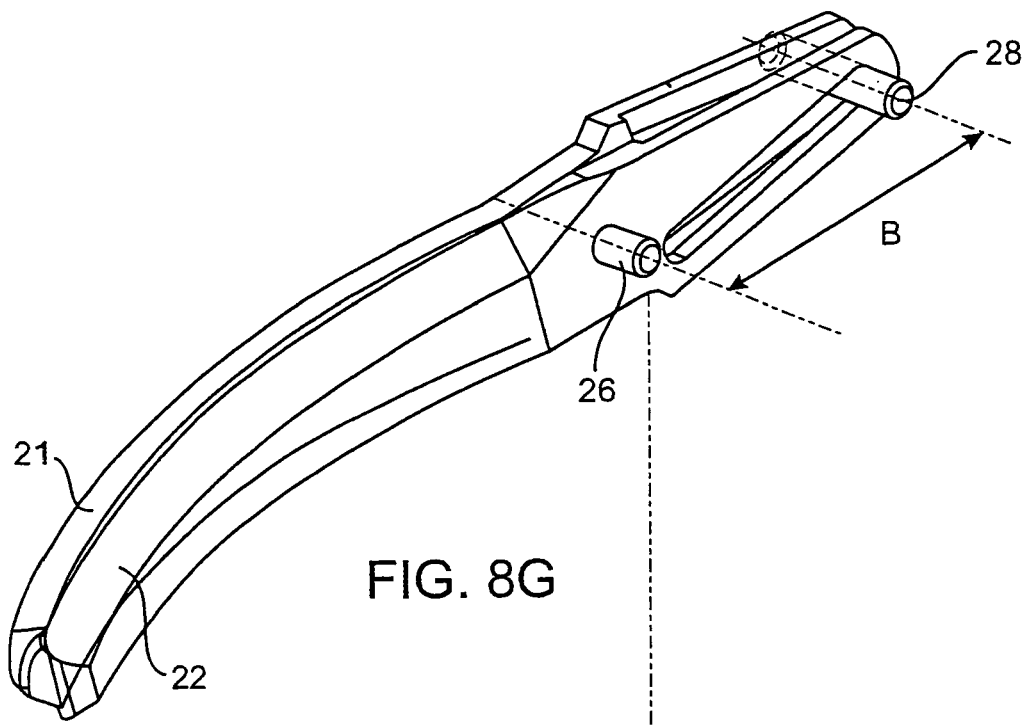
Figure 8H:
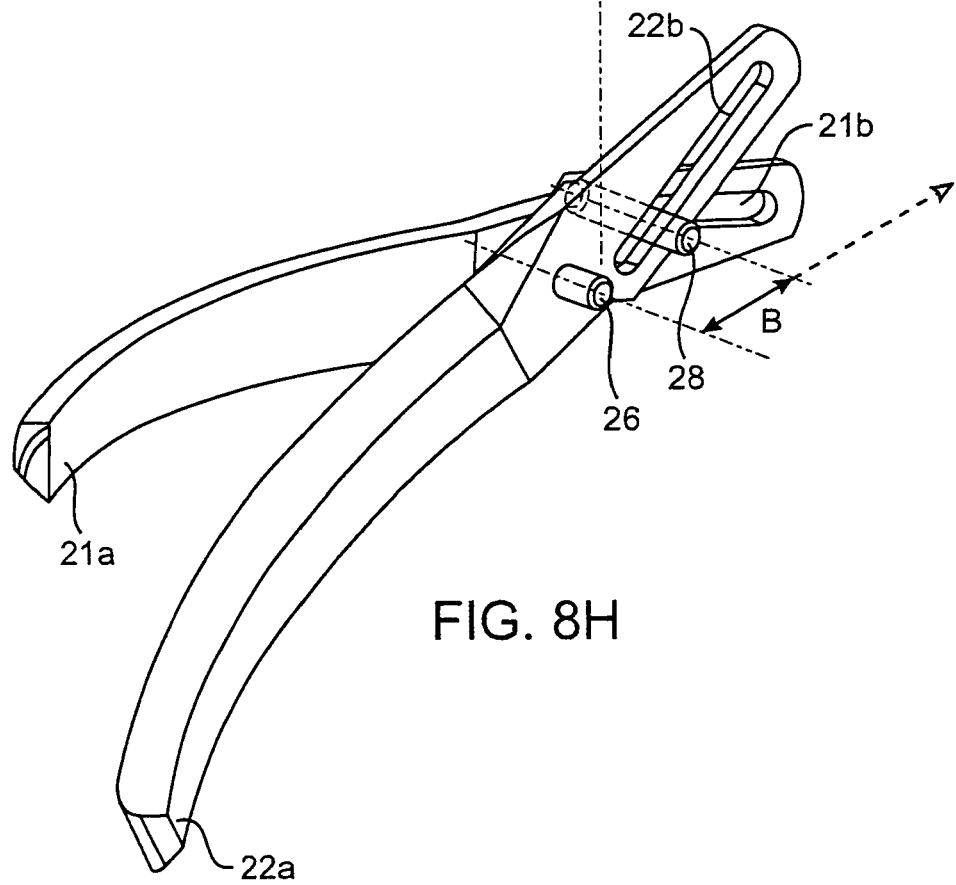

With reference to FIGS. 8A-8H, each blade 21, 22 has a corresponding generally longitudinal slot 21b, 22b in the proximal portion of each blade. Slots 21b and 22b are at the opposite blade end from distal shear portions 21a and 22a (see FIGS. 8A and 8H). Connector 31 couples to each blade by engagement pin 28 which passed through both of slots 21b, 22b and has an axis generally parallel and proximal to pivot 26 (see FIGS. 8B and 8G). The slots 21b, 22b are angularly offset from pin 26, so that the line extensions of the slots do not pass through pin 26. As a result, the core 30, and connector 31 slide longitudinally as shown by Arrow E in FIG. 8E. The pin 28 slides along slots 21b, 22b in a cam-slot engagement as shown by Arrow B in FIGS. 8G and 8H, causing the blades to rotate about pin 26. As core 30 and connector 31 slide proximally, the blades close upon one another in a shearing action as shown in FIG. 8F. As core 30 and connector 31 slide distally, the blades open apart from one another, as shown by Arrow H in FIG. 8D. The connector 31, pin 28, and blades 21, 22 preferably comprise conductive materials, such as stainless steel and the like, so as to provide a conduction path. The blades 21 and 22 may be straight or curved at the shearing surfaces thereof (e.g., curved Metzenbaum blades).

Referring back to FIG. 7A, shaft 16 is received in a roll bearing housing 33 mounted in the distal (front) end of the tool base 12. Core 30 extends further through bearing housing 33 to adjacent the proximal (rear) end of the tool base 12. An actuator bar or rotating link 32 is pivoted to base 12 on one side of the core 30 at a pivot assembly 34, and extends over and generally perpendicular to core 30. The core 30 couples to the medial portion of the actuator bar 32 by engagement of journal pin 55. Bar 32 in turn engages an eccentric actuator assembly 36 which is mounted to base 12 at the opposite side of core 30. Rotary action of the eccentric actuator assembly, which is further described below with reference to FIGS. 14A-14H, causes the bar 32 to pivot back and forth about pivot 34 as depicted by arrow F. This motion in turn causes a pivotal movement of journal 55 through a generally longitudinal range of motion, as depicted by arrow G, so as to cause a longitudinal back and forth motion of core 30. The movement of core 30 and connector rod 31 in turn opens and closes the blades 21 and 22.

Referring now to FIGS. 9A-9C and 10-10C, the core rod or actuator rod assembly 30 of the electrosurgical instrument is illustrated. The core rod assembly 30 generally comprises a distal tip portion 40, an intermediate mid portion 41, and a proximal base portion. As shown best in FIGS. 9A and 10A, a core base 42 is rotatably mounted to mid portion 41 by slot 42a. An intervening electrically insulating material 39 isolates the mid portion 41 from the core base 42 and pins 43. Alternatively, the mid portion 41 may comprise an insulating material. One or more pins 43 or equivalent fastening means may be used to mount the core portions 40 and 41 together. One or more pins 43b or equivalent fastening means are aligned with slot 42a to allow rotation and coupling of core portions 41 and 42. To provide a safe and effective conduction path that minimizes unintended current leakage, the end effector housing 24 and shaft 16 preferably comprise or may be covered with an insulating material as well. Suitable insulative materials include polymeric materials such as Polymed II and Ultem. The distal core tip 40 is fixedly attached to midportion 41 and preferably comprises a conductive material, such as stainless steel and the like.

With reference to FIGS. 9B, 9C, and 10A, an insulated conductor 48 passes longitudinally adjacent core 30, extending distally from the tool base 12, to pass through a hole or slot 47 to electrically connect to the core tip portion 40 by crimping engagement or other equivalent means with an electrical connector 49. Preferably, the conductor 48 passes in a plurality of spiral loops about the core rod 30 to permit free rotation of the core rod 30 relative to the tool base 12. Pin 43a is used as a stress or strain release as the conductor is spirally wrapped around pin 43a, as shown in FIGS. 9A. With reference to FIG. 10C, holes 41a, 41b, 41c in the midportion 41 are engaged by pins 43a, 43b, and 43 respectively. Hole 41d is aligned with slot 16a on the shaft 16 (FIG. 4A) for receiving a pin (not shown) which allows rotation of the core rod with the shaft.

Referring now to FIGS. 11A and 11B, core assembly 30 positioning within the shaft 16 of the electrosurgical instrument 10 is illustrated. Both the core assembly 30 and the insulated conductor 48 are housed within the shaft 16. The shaft in turn is mounted to the tool base 12, preferably by means of the journal bearing assembly 33 and a receiver 80 so as to permit actuation of a rotational degree of freedom relative to tool base 12.

Referring now to FIGS. 12A-12F, the bayonet assembly 14b is further illustrated. The bayonet assembly connects the end effector 14 to the shaft 16 and the actuator or core rod 30. The bayonet assembly permits the end effector 14 to be conveniently mounted and de-mounted, e.g., for replacement or refurbishing. It will be appreciated that equivalent alternative releasable mounting means may be employed, or an integral or permanent mounting may be used. The tip connector 31 includes an angled proximal engagement slot 31b opposing a distal engagement pin 45 of the core tip 40. Similarly, a coordinately aligned pair of angled proximal slots 24b in end effector housing 24 oppose a pair of distal engagement pins 51 in the distal end of the shaft 16. As the end effector 14 is inserted against shaft 16, as shown by Arrow I, the slots 31b and 24b engage pins 45 and 51 respectively as shown in FIGS. 12A, 12E, and 12F. The pins may then be locked by rotating the housing 24 to move the pins to the angled portion, as shown by Arrow J in FIG. 12B. Pin 51 fits into an undercut formed by slot 24b of the housing, as shown in FIG. 12F. The housing 24 may then be additionally fixed, such as by locking pin 53a which engages housing 24 and shaft holes or slots 53b (see FIG. 12C) or by an equivalent locking mechanism, such as a set screw, a firm slot/pin snap-fit, or like mechanism.

Figure 13A:
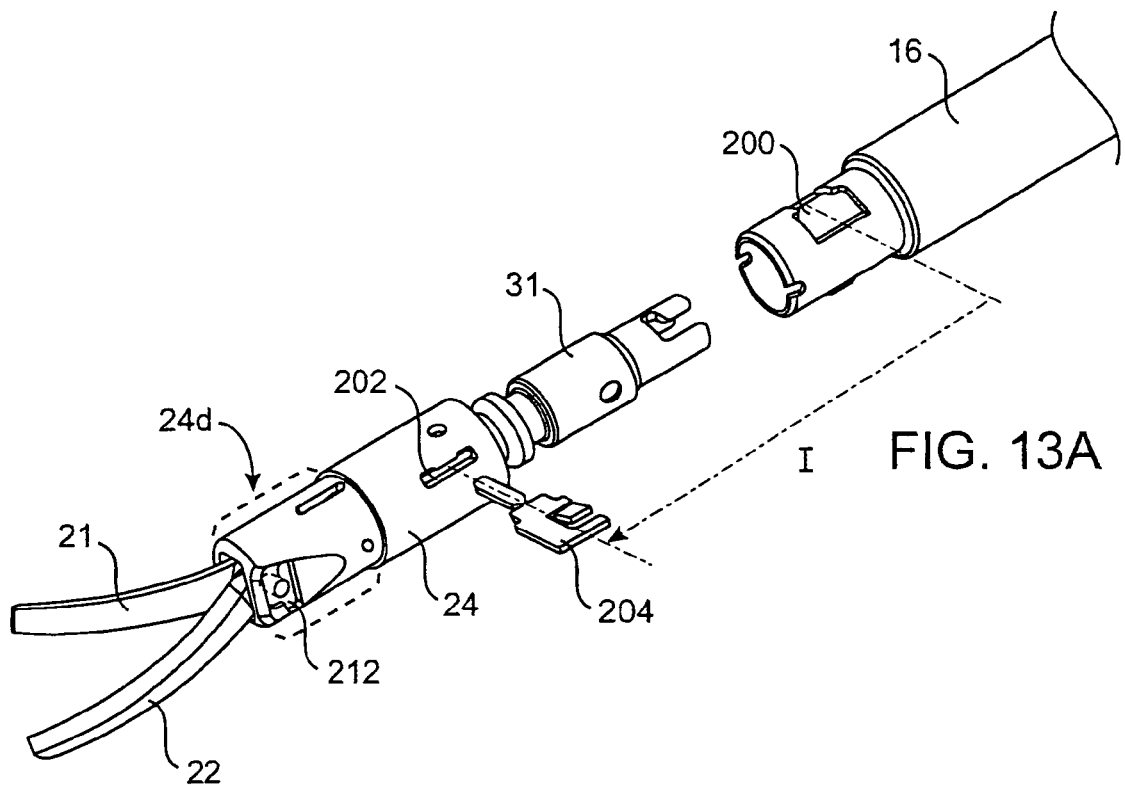
FIGS. 13A-13E illustrate an alternative assembly of the distal portion of the instrument of FIG. 4A.
Figure 13B:
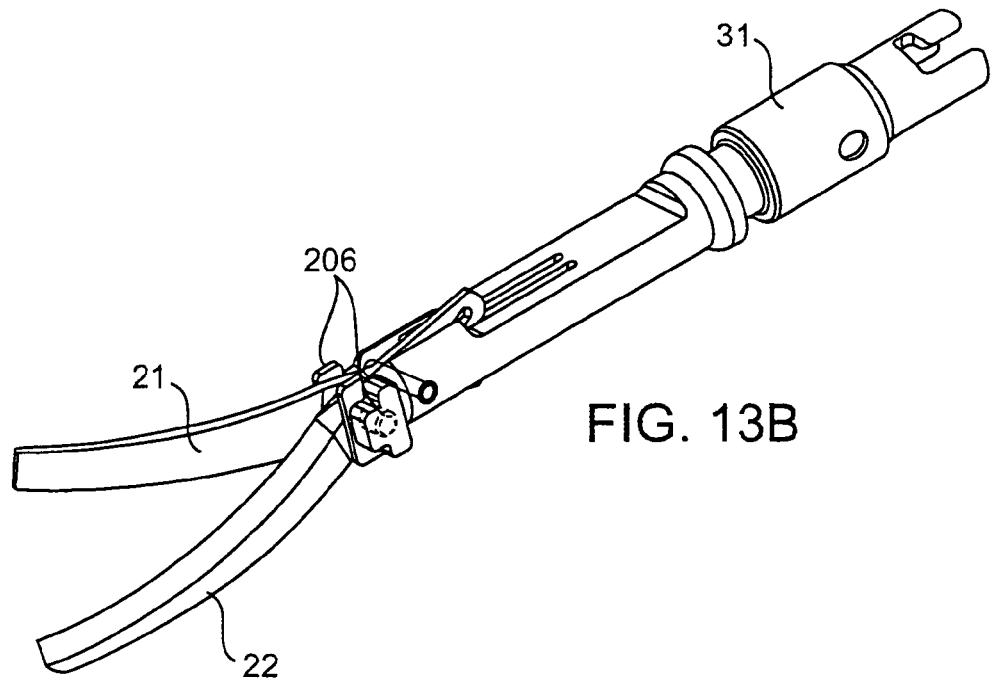
Figure 13C:
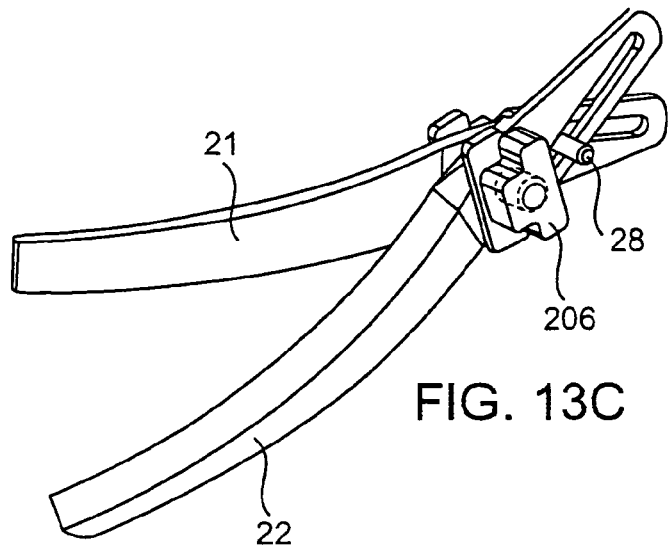
Figure 13D:
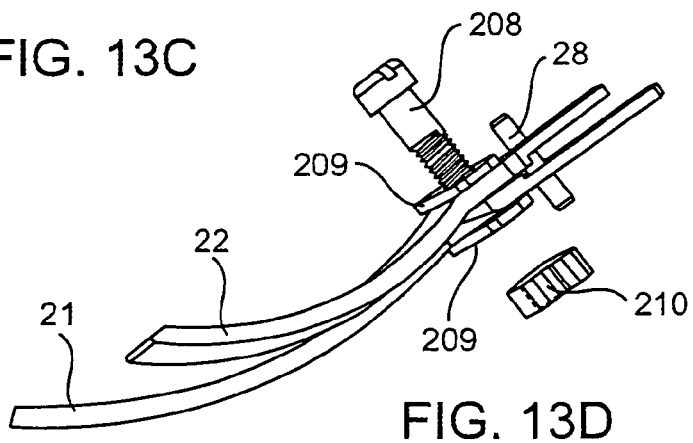
Figure 13E:
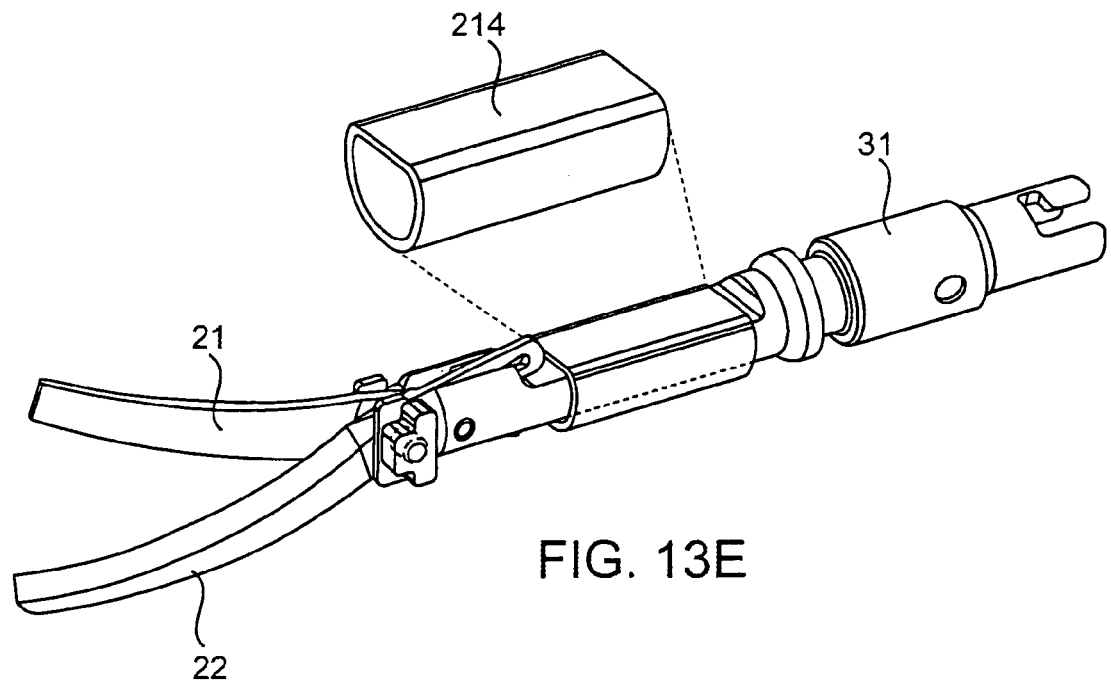

Referring now to FIGS. 13A-13E, an alternative bayonet assembly is illustrated. In particular, as shown by FIG. 13A, the distal end of the shaft 16 includes a pin slot 200 opposing another pin slot 202 in the housing 24. The end effector 14 is inserted against shaft 16, as shown by Arrow I, and slots 200 and 202 are engaged by a bent locking pin 204 so as to effectively fix the housing 24 to the shaft 16. FIGS. 13B, 13C, and 13D further illustrate a modified pivot mount 206 of the blades 21 and 22. The blades 21 and 22 are co-axially pivoted to the tip housing 24 by means of a pivot bolt 208 that fastens the blades between a pair of washer plates 209 and is secured by a pivot nut 210 that fits into a second housing slot 212. FIG. 13E illustrates that an insulative material or insulative shrinkable sleeve 214 may be disposed over the connector rod 31 to further prevent unintended current leakage. In addition, insulation 24d which may be heat shrinkable may be disposed over the distal tip of the housing 24 as seen in FIG. 13A.

Referring now to FIGS. 14A-14D, preferred coupling of the actuator or core rod 30 to the tool base 12 is illustrated.

Figure 14B:
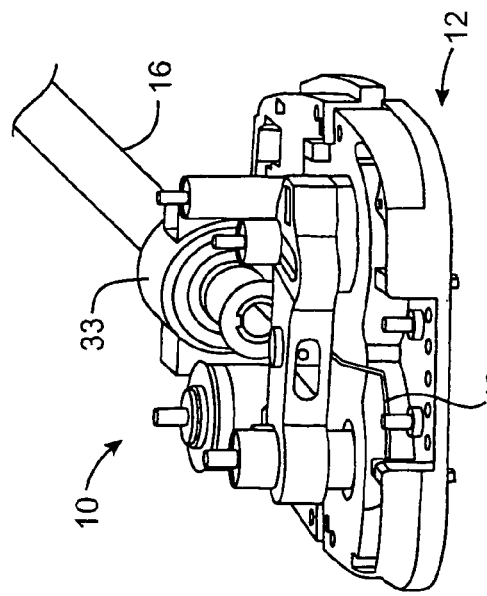
FIGS. 14A-14H illustrate exploded views of the proximal portion of the instrument of FIG. 4A, with a cover of a tool base removed to show internal structures of the tool base.
Figure 14D:
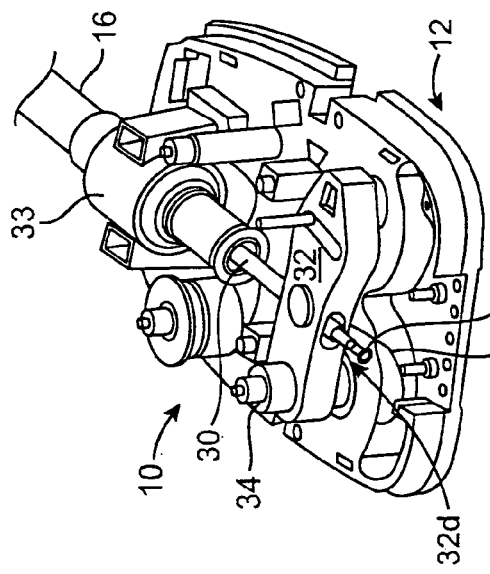
Figure 14A:
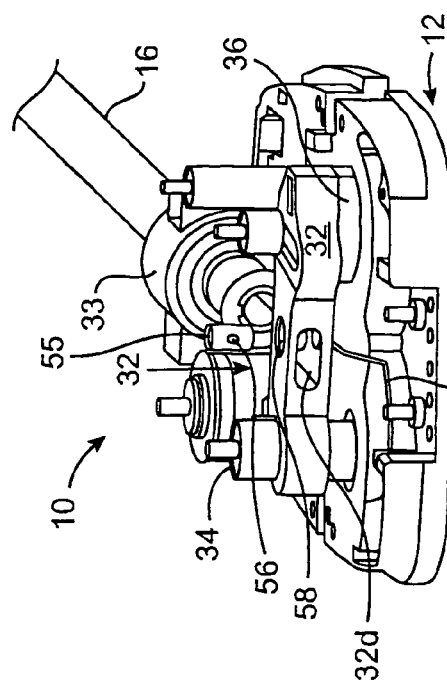
Figure 14C:
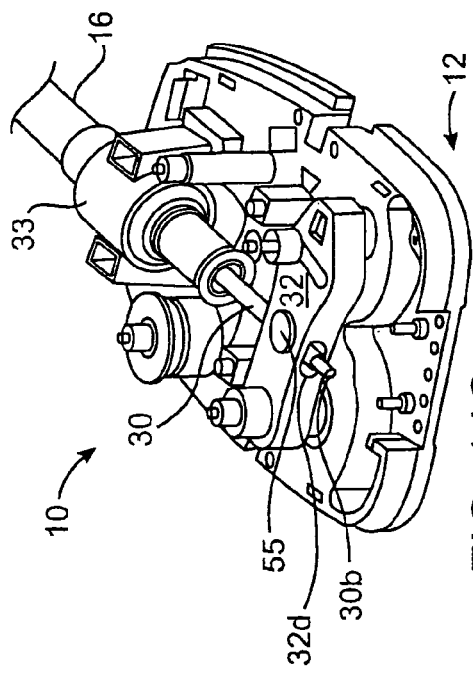

The core rod 30 extends further through bearing housing 33 to adjacent the proximal (rear) end of the tool base 12. The actuator bar or rotating link 32 is pivoted to the tool base 12 on one side of the core rod 30 at pivot assembly 34, and extends over and generally perpendicular to the core rod 30. A shown in FIG. 14A, the core rod 30 couples to a medial portion of the bar 32 by engagement of a journal pin 55, passing through an aperture 56 in the pin 55. The journal pin engages the bar 32 via slot or opening 58. The proximal core rod tip 30b is stopped by a locking nut 59 which bears on the proximal surface of the pin 55, preventing sliding of core rod 30 through aperture 56, as best seen in FIG. 14D. A slot 32d in the side of the actuator bar 32 permits the link to rotate independent of core rod 30 through a range of motion, as pin 55 pivots with respect to the actuator bar 32 (see FIG. 14C). The insulated conductor 48 passes out from the shaft 16 adjacent core 30 and under bar 32 to the rear of base 12 to an electrical connector for connection to an electrosurgical generator, as shown in FIG. 14B.

With reference to FIGS. 14E through 14H, the rotating bar 32 engages an eccentric actuator assembly 36 which is mounted to the tool base 12 at an opposite side of the core 30 and is rotatable about an axis A36. An actuator disk 60 is concentrically aligned and fixed to pivot shaft assembly 36a and is rotatable about the axis A36 through a transmission member (not shown) by actuator drivers of the robotic surgical system (see FIG. 1). The eccentric cam pin 60 is mounted off center on a disk or eccentric cam wheel 68, generally parallel to shaft 36. The eccentric pin 60 extends through a radial slot 32c (radial to pivot A34) to slidably engage the actuator bar 32 within a selected range of motion. Actuator shaft 36 extends through a clearance slot 32b (concentric to pivot A34) to slidably engage the actuator bar 32 within a selected range of motion. As a result, as disk 68 is actuated to rotate in the direction shown by Arrow K, pin 60 bears on slot 32c so as to cause the actuator bar 32 to rotate as shown by Arrow L. Engagement of pin 55 causes the actuator or core rod 30 to translate longitudinally as shown by Arrow M. This lever arm relationship results in a smaller longitudinal movement of pin 55 than of bar slot 32c, in this case approximately one-half or less, and thus provides a mechanical advantage. This motion is reversibly controllable by the robotic surgical system.

Figure 14E:
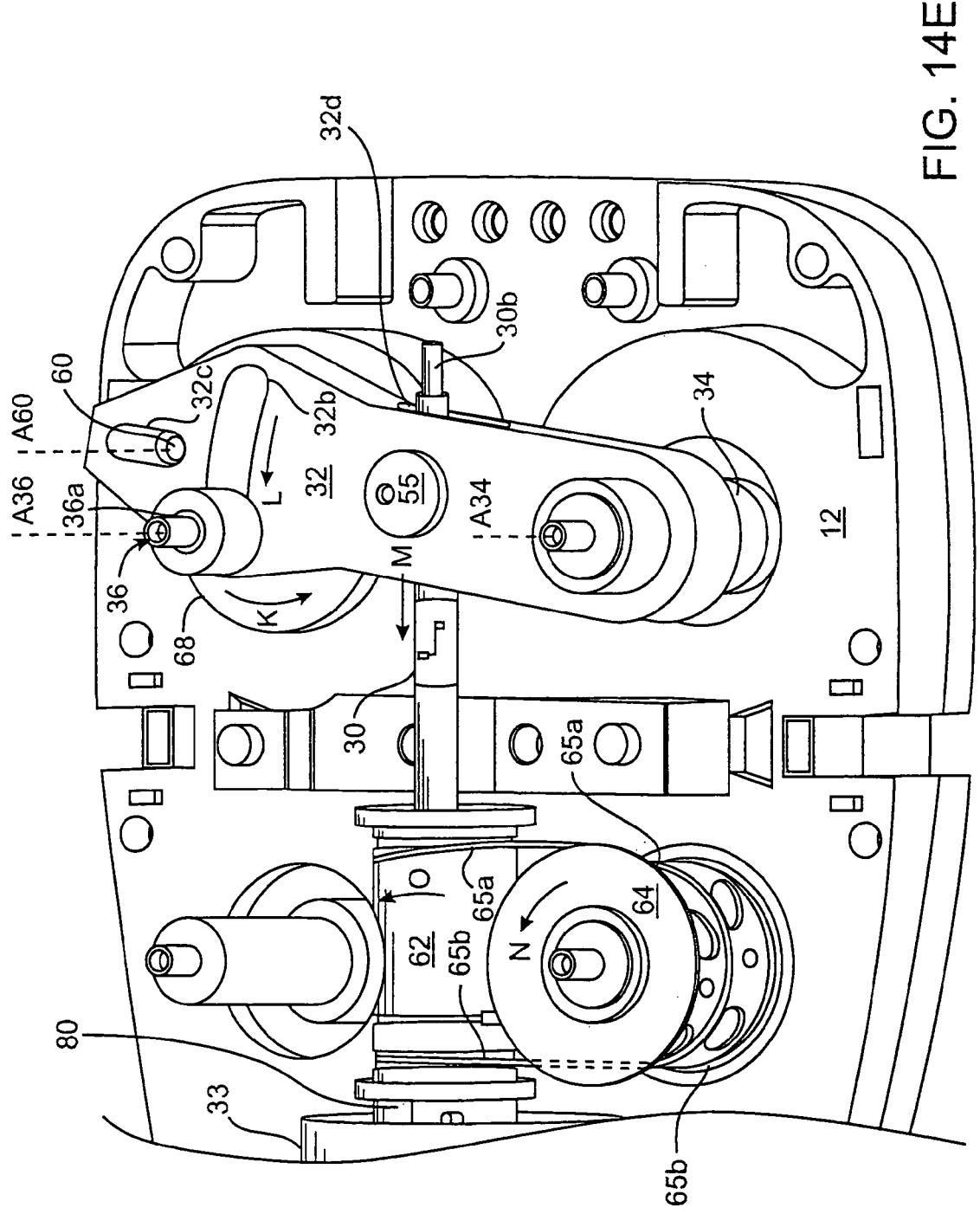
Figure 14F:
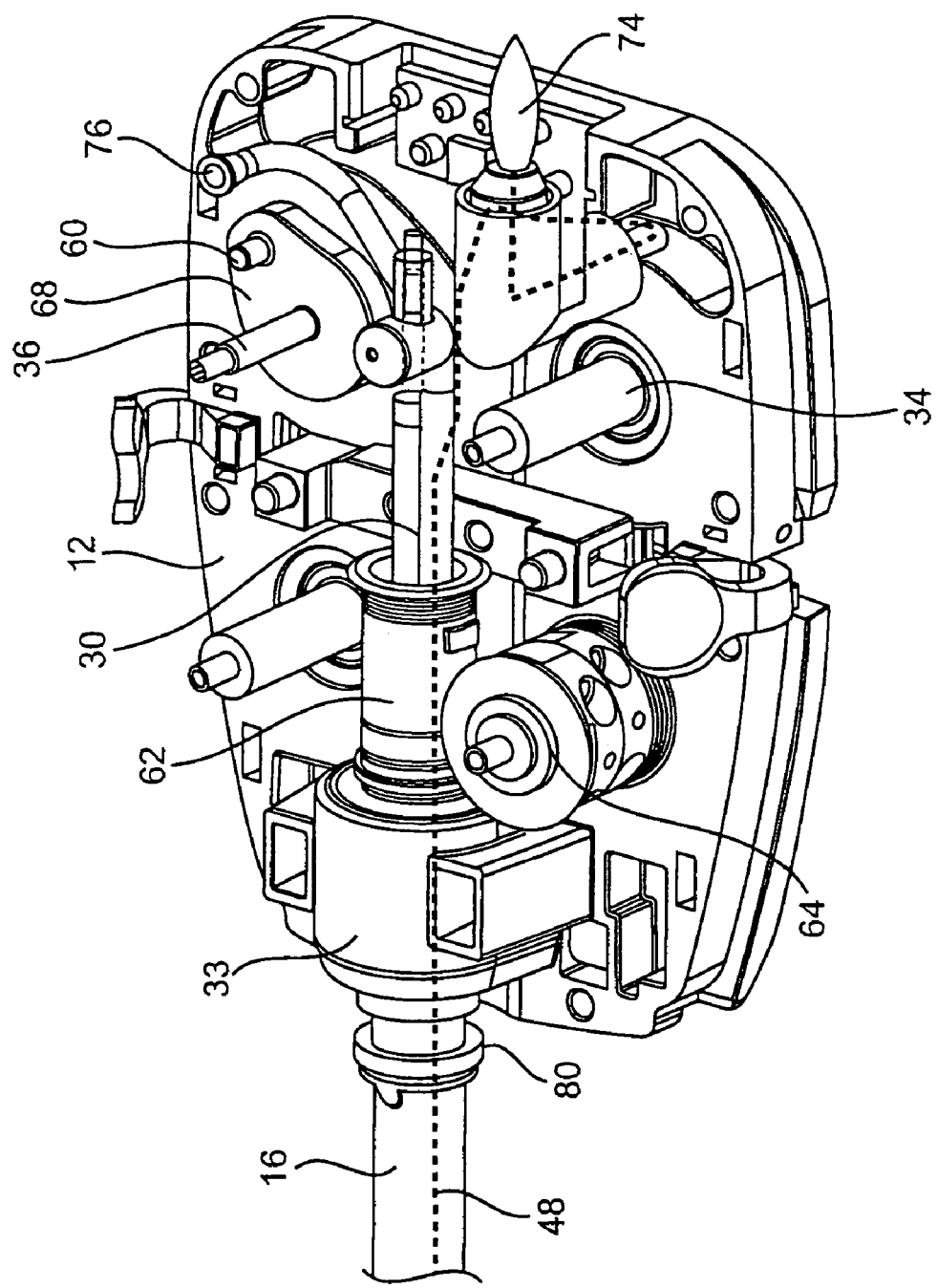
Figure 14G:
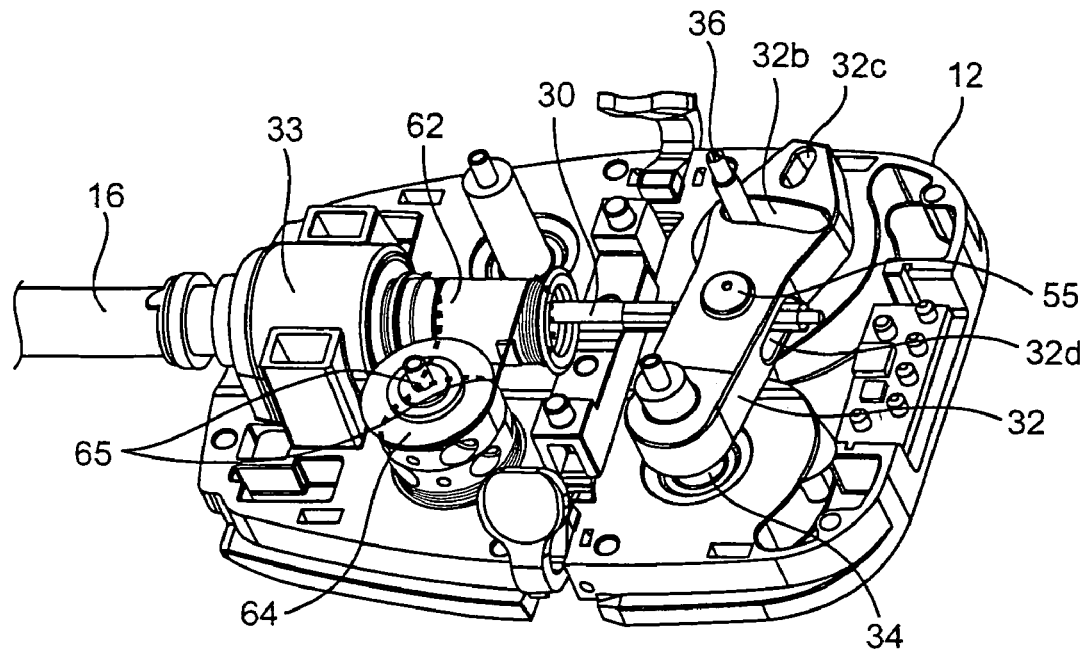
Figure 14H:
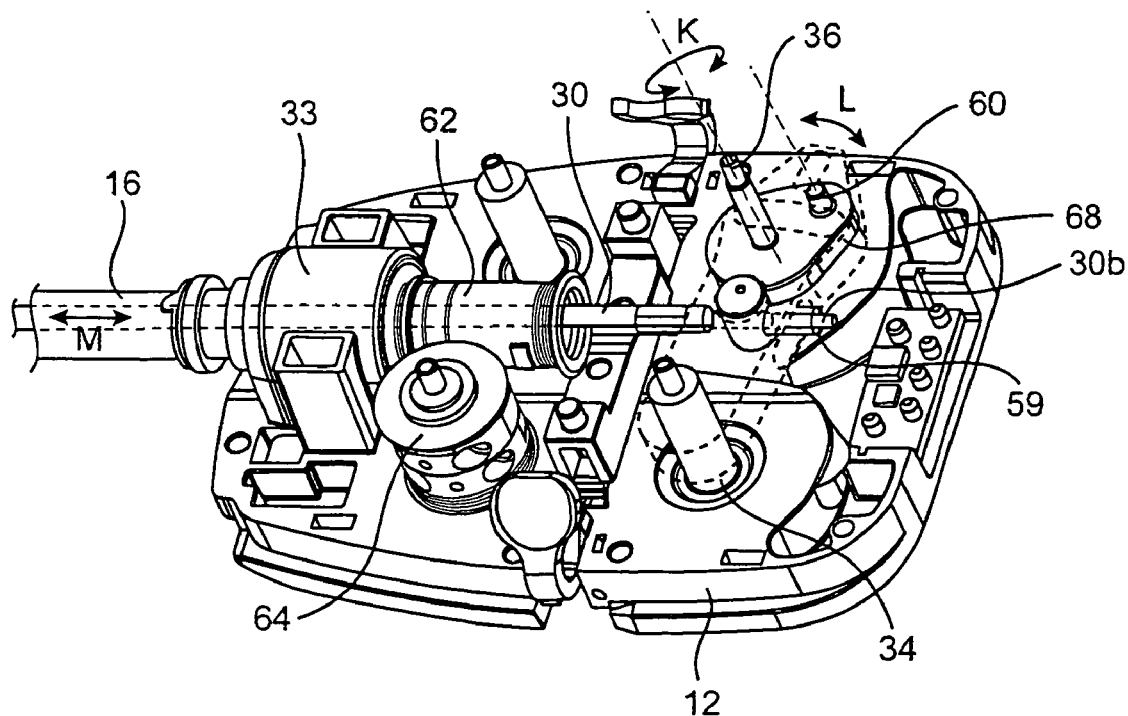

FIGS. 14E and 14G further show the rotational actuation of shaft 16 via receiver 80. A drum 62 is mounted parallel to and surrounding receiver 80, arranged adjacent a rotational actuator spool 64 which is pivotally mounted generally perpendicularly to core rod 30. A cable 65 has an upper cable portion 65a which wraps around both the drum 62 and the spool 64 and a lower cable portion 65b which wraps around the spool and the drum in the opposite direction. Like actuation shaft 36, the spool 64 is rotatable through a transmission member (not shown) by actuator drivers of the robotic surgical system. As a result, as spool 64 is actuated to rotate in the direction shown by Arrow N in FIG. 14E, cables 65a, 65b wind/unwind respectively from drum 62, causing the drum 62 together with the receiver 80, shaft 16, and core 30 to rotate, as shown by Arrow O. This motion is reversibly controllable by the robotic surgical system.

Figure 15B:
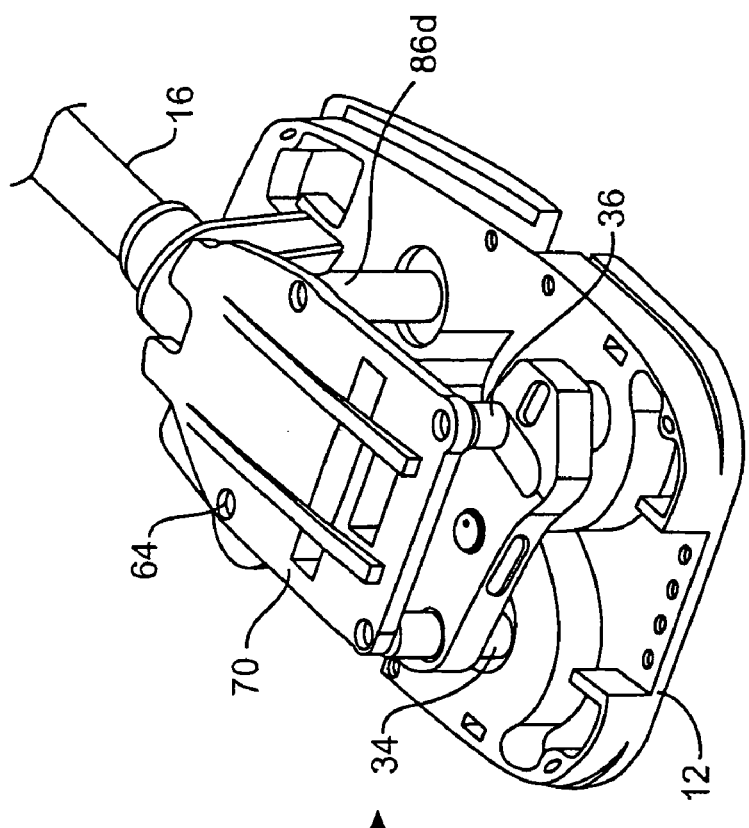
FIGS. 15A and 15B illustrate further exploded views of the proximal portion of the instrument of FIG. 4A, with a chassis over the tool base.
Figure 15A:
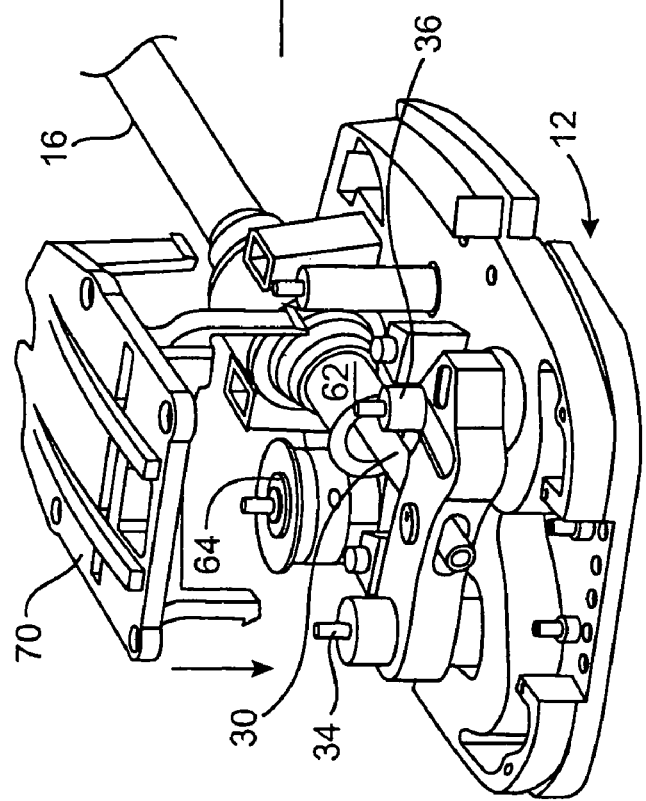
Figure 17A:
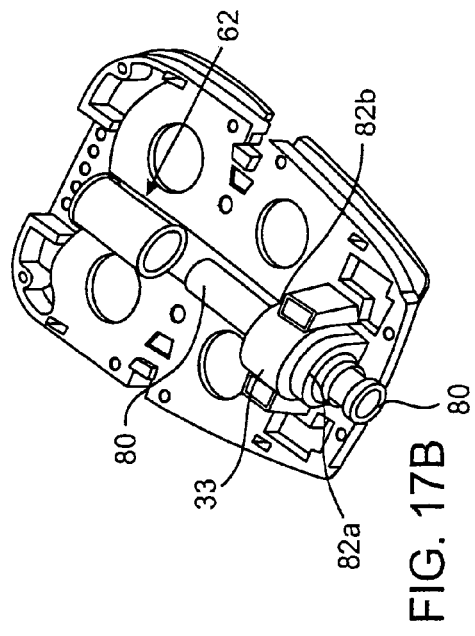
Figure 17B:
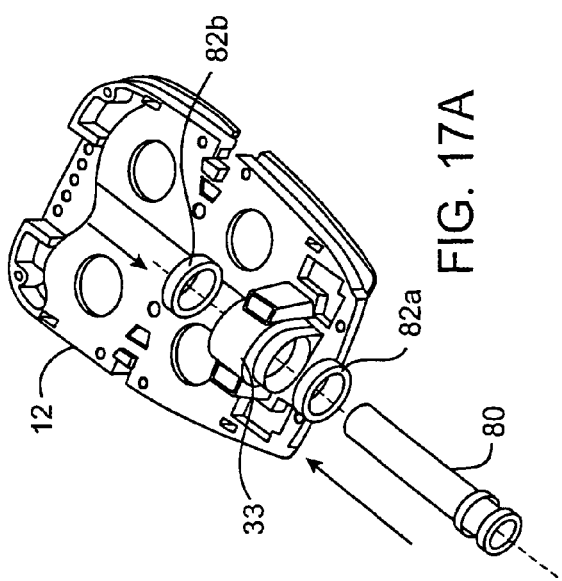
Figure 17C:
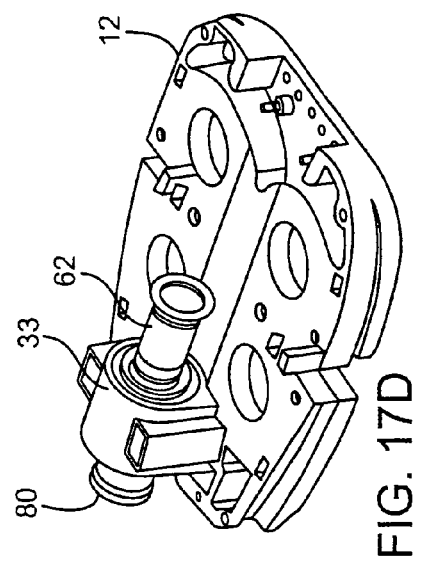
Figure 17D:
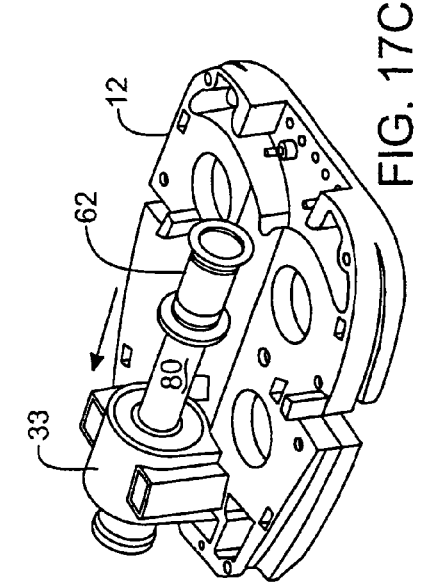
Figure 19A:
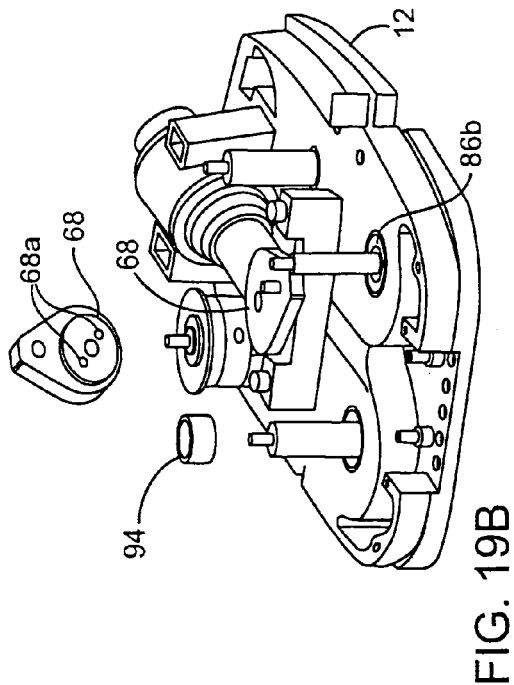
Figure 19B:
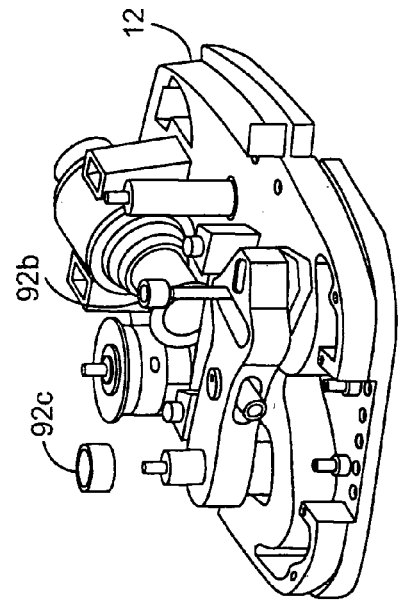
Figure 19C:
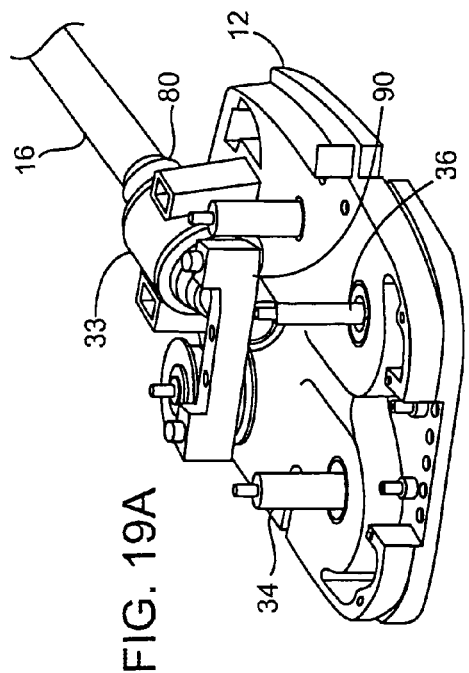
Figure 19D:
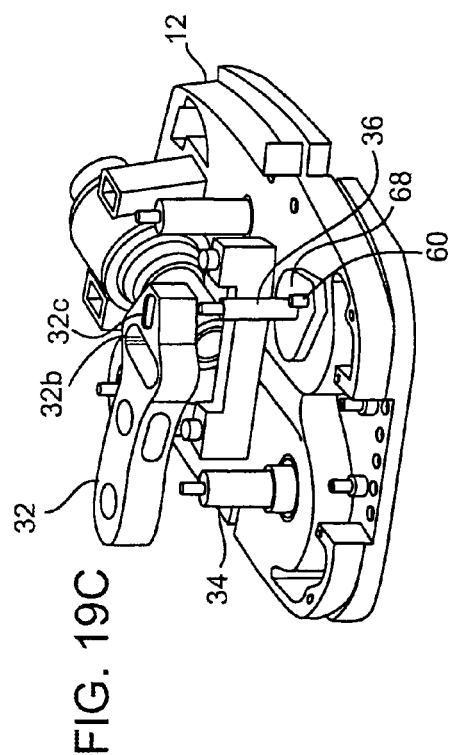

Referring now to FIGS. 15A and 15B, a chassis 70 supports the ends of the tool base shafts, including pivots 34, 36, and 64. It will be appreciated that the illustrated tool base 12 is an embodiment with generic features capable of supporting a number of different alternative robotic tool types. For example, shaft or post 86d can be substituted for actuator elements, if additional degrees of freedom or actuation functions are desired.

Referring now to FIGS. 16A-16C, an optional flush tube 76 may be mounted to a tool base cover 72 by a flush port 78 and the assembled base 12. The flush tube preferably extends forward (distally) within the base 12 to communicate with the shaft 16 to permit fluids to be passed through the shaft 16 and/or to pressurize the shaft 16. For example, introduction of insufflation gas during surgery or the introduction of cleaning or sterilization gases or fluids prior and/or subsequent to surgery may be passed to the shaft 16 via flush tube 76. U.S. Pat. No. 6,004,509 describes the use of fluids and gases to maintain sterility of a surgical instrument, and is incorporated herein by reference.

With reference to FIGS. 16D and 16E, the base cover 72 mounts an electrical connector 74, in this case banana clip assembly 74a, 74b, and 74c, for the insulated conductor 48 to permit connection to an electrosurgical generator. Note that the connections described above provide an insulated continuous electrical path from the base connector 74 to the scissors blades 21 and 22, protected from tissue contact except at the blades 21, 22. Energization of the blades is controllable by the surgeon as described above.

Referring now to FIGS. 17A-17D, 18A-18D, and 19A-19D, perspective illustrations of the tool base in progressive stages of assembly are depicted. FIGS. 17A-17D illustrate installation of roll bearings 82a and 82b, the receiver 80, and the drum 62. FIGS. 18A-18D show installation of actuator bearings 84a, 84b, 84c, and 84d, actuator shafts 86a, 86b, 86c, and 86d, actuator spool elements 64a and 64b, and actuator cables 65a and 65b. FIGS. 19A-19D illustrate installation of a medial bar 90, the actuator disk 68 and a lower link bearing 94, the actuator bar or link 32, and upper link bearings 92a and 92b.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Therefore, the above description should not be taken as limiting the scope of the invention which is defined by the appended claims.

What is claimed is:

1. A method of performing a robotic surgical procedure, the method comprising:

connecting a surgical instrument to a robotic surgical system, the surgical instrument having an elongate shaft, at one end of which an end effector is mounted;

passing the end effector of the surgical instrument through an entry port in a patient body;

engaging tissue with the end effector, the tissue being engaged between a pair of blades of the end effector;

shearing the tissue cooperatively between the blades by transmitting at lease one force from an interace member on the robotic surgical system to a first rotable shaft on the surgical instrument, the first rotable shaft engaging a rotating link pivoted at a second shaft, the rotating link coupling an actuator rod, the actuator rod engaging a connecting rod, the connecting rod engaging each blade, wherein the at least one force causes the first rotatable shaft to rotate so as to cause the rotating link to pivot at the second shaft, the actuator rod to move in a tangential direction with a point on the rotating link, and the actuator rod and connector rod to move at least one of the blades; and delivering electrical energy to the tissue engaged by the blades.

2. A method as in claim 1, wherein delivering electrial energy comprises transmitting electrical energy to at least one blade from a conductor.

3. A method as in claim 2, further comprising connecting an external electrosurgical generator to the conductor.

4. A method as in claim 2, further comprising preventing unintended current leakage by insulating the conductor within the elongate shaft.

5. A method as in claim 2, further comprising preventing unintended current leakage by extending the conductor to a distaltip of the actuator rod slidably housed within the shaft.

6. A method as in claim 5, wherein the distal tip of the actuator rod and the connector rod transmit electrical energy to the at least one blade from the conductor, and wherein unintended current leakage is further prevented by insulating the connector rod within a housing supporting the pair of blades and connectable to a distal end of the shaft.

7. A method as in claim 6, wherein unintended current leakage is further prevented by insulating the connector rod with an insulation sleeve.

8. A method as in claim 1, wherein delivering electrical energy is carried out before, during, and/or after tissue shearing.

9. A method as in claim 1, wherein the delivered electrical energy produces heat capable of treating the tissue.

10. A method as in claim 1, further comprising cauterizing the tissue with the delivered electrical energy.

11. A method as in claim 1, further comprising coagulating blood with the delivered electrical energy.

12. A method as in claim 1, wherein delivering electrical energy is carried out in a monopolar fashion.

13. A method as in claim 1, wherein the delvered energy comprises radio frequency energy.

14. A method as in claim 1, further comprising rotating the elongate shaft relative to a tool base of the surgical instrument about an axis defined from a proximal end to a distal end of the elongate shaft.

15. A method as in claim 1, wherein connecting the surgical instrument to a robotic surgical system includes releasably mounting the surgical instrument on a robotically controlled arm.

* * * * *